United States Patent
Strom et al.

(10) Patent No.: US 7,834,152 B2
(45) Date of Patent: *Nov. 16, 2010

(54) ANTAGONISTS OF INTERLEUKIN-15

(75) Inventors: Terry B. Strom, Brookline, MA (US); Wlodzimierz Maslinski, Warsaw (PL)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/726,086

(22) Filed: Mar. 20, 2007

(65) Prior Publication Data

US 2008/0008680 A1 Jan. 10, 2008

Related U.S. Application Data

(63) Continuation of application No. 10/245,243, filed on Sep. 17, 2002, now Pat. No. 7,258,853, which is a continuation of application No. 09/437,585, filed on Nov. 9, 1999, now Pat. No. 6,451,308, which is a continuation-in-part of application No. 08/842,947, filed on Apr. 25, 1997, now Pat. No. 6,001,973.

(60) Provisional application No. 60/016,634, filed on Apr. 26, 1996.

(51) Int. Cl.
*C07K 14/54* (2006.01)
*C12N 15/62* (2006.01)

(52) U.S. Cl. .................... 530/351; 530/402; 435/69.52; 435/69.7

(58) Field of Classification Search ........................ None
See application file for complete search history.

(56) References Cited

U.S. PATENT DOCUMENTS

| | | | |
|---|---|---|---|
| 5,011,684 A | 4/1991 | Strom | |
| 5,116,964 A | 5/1992 | Capon | |
| 5,262,522 A | 11/1993 | Gearing | |
| 5,552,303 A | 9/1996 | Grabstein | |
| 5,574,138 A | 11/1996 | Grabstein | |
| 5,707,616 A | 1/1998 | Grabstein | |
| 5,747,024 A | 5/1998 | Grabstein | |
| 5,892,001 A | 4/1999 | Grabstein | |
| 6,001,973 A * | 12/1999 | Strom et al. | 530/351 |

FOREIGN PATENT DOCUMENTS

| | | |
|---|---|---|
| CA | 2210491 | 8/1996 |
| WO | WO 88/07089 | 9/1988 |
| WO | WO 95/27722 | 10/1995 |
| WO | WO 96/04306 | 2/1996 |
| WO | WO 96/26274 | 8/1996 |

OTHER PUBLICATIONS

Mikayama et al. Proc. Natl. Acad. Sci. USA vol. 90, pp. 10056-10060.*
Voet et al. Biochemistry John Wiley & Sons, Inc., pp. 126-128 and 228-234.*
Ajjan et al., "Detection of IL-12, IL-13, and IL-15 Messenger Ribonucleic Acid in the Thyroid of Patients with Autoimmune Thyroid Disease", *J. Clin. Endocrinol. Metab.*, 82(2):666-669, 1997.
Akatsuka et al., "Synovial Mononuclear Cells Consist with T Cells Which Produce High Levels of Tumor Necrosis Factor α", *Microbiol. Immunol.*, vol. 41, (1997) pp. 367-370.
Ameglio et al., "Anti-intercellular substance antibody log titres are correlated with serum concentrations of interleukin-6, interleukin-15 and tumor necrosis factor-alpha in patients with *Pemphigus vulgaris* relationships with peripheral blood neutrophil counts, disease severity and duration and patients' age", *J. Biol. Regul. Homest. Agents*, 13(4):220-224, 1999.
Anderson et al., Functional Characterization of the Human Interleukin-15 Receptor α Chain and Close Linkage of IL15RA and IL2RA Genes, *J. Bio. Chem.* 270:29862-29869 (1995).
Aringer et al., "Serum interleukin-15 is elevated in systemic lupus erythematosus", *Rheumatology* (Oxford) 40(8):8760881, 2001.
Armitage et al., "IL-15 Has Stimulatory Activity for the Induction of B Cell Proliferation and Differentiation", *J. Immunology*, vol. 154 (1995) pp. 483-490.
Baan et al., "Increased intragraft IL-15 mRNA expression after liver transplantation", *Clin. Transplant.* 12(3):212-218, 1998.
Baan et al., "The Macrophage-Derived T-Cell Growth Factor Interleukin-15 Is Present in Interleukin-2-Independent Rejection After Clinical Heart and Liver Transplantation", *Transplant Proc.* 31(7):2726-2728, 1999.
Baan et al., "Anti-CD25 Therapy Reveals the Redundancy of the Intragraft Cytokine Network After Clinical Heart Transplantation", *Transplantation* 67(6):870-876, 1999.
Bamford et al., The interleukin (IL) 2 receptor β chain is shared by IL-2 and a cytokine, provisionally designated IL-T, that stimulates T-cell proliferation and the induction of lymphokine-activated killer cells, *Proc. Nat. Acad. Sciences*, 91:4940-4944 (1994).
Blanar et al., "Interaction Cloning: Identification of a Helix-Loop-Helix Zipper Protein That Interacts with c-Fos", *Science*, 256:1014-1018 (1992).
Brekke et al., "Structure-Function Relationships of Human IgG", *The Immunologist*, vol. 2 (1994) pp. 125-130.
Burger et al., "Imbalance between interstitial collagenase and tissue inhibitor of metalloproteinases 1 in synoviocytes and fibroblasts upon direct contact with stimulated t lymphocytes", *Arthritis & Rheumatism*, vol. 41 (1998).
Burton et al., "A lymphokine, provisionally designated interleukin T and produced by a human adult T-cell leukemia line, stimulates T-cell proliferation and the induction of lymphokine-activated killer cells", *Proc. Nat. Acad. Sciences*, 91:4935-4939 (1994).
Carson et al., "Interleukin (IL) 15 Is a Novel Cytokine That Activates Human Natural Killer Cells via Components of the IL-2 Receptor", *J. Exper. Medicine* 180:1395-1403 (1994).
Carson, "Unconventional T-cell activation by IL-15 in rheumatoid arthritis", *Nature Med.* 3(2):148-149, 1997.
Chae et al., "Mutant IL-15 Protein Exerting Antagonistic Effects on IL-15 Triggered Cell Proliferation", *J. American Society of Nephrology* 7:1654 (1996).

(Continued)

*Primary Examiner*—Prema Mertz
(74) *Attorney, Agent, or Firm*—Fish & Richardson P.C.

(57) ABSTRACT

Disclosed herein are mutant IL-15 polypeptides and methods for using these polypeptides to modulate the immune response in a patient.

20 Claims, 19 Drawing Sheets

OTHER PUBLICATIONS

Chae et al., "Distribution of IL-15 Receptor α-Chains on Human Peripheral Blood Mononuclear Cells and Effect of Immunosuppressive Drugs on Receptor Expression", *The Journal of Immunology*, 157: 2813-2819 (1996).

Courtenay et al., "Immunisation against heterologous type II collagen induces arthritis in mice", *Nature* 283:5748 (1980).

Cunningham et al., "High-Resolution Epitope Mapping of hGH-Receptor Interactions by Alanine-Scanning Mutagenesis", *Science*, 244, 1081-1085 (1989).

Elliott et al., "Randomised double-blind comparison of chimeric monoclonal antibody to tumour necrosis factor alpha (cA2) versus placebo in rheumatoid arthritis.", *Lancet*, 344:8930:1105-10 (1994).

Elliott et al., "Repeated therapy with monoclonal antibody to tumour necrosis factor alpha (cA2) in patients with rheumatoid arthritis.", *Lancet* 344:8930:1125-27 (1994).

George et al., "Current methods in sequence comparison and analysis", *Macromolecular Sequencing and Synthesis Selected methods and Applications*, pp. 127-149 (1988).

Giri et al., "IL-15, A Novel T Cell Growth Factor That Shares Activities and Receptor Components with IL-2", *J. Leukocyte Biology*, 57:763-766 (1995).

Giri et al., "Identification and cloning of a novel IL-15 binding protein that is structurally related to the α chain of the IL-2 receptor", *EMBO Journal* 14:3654-3663 (1995).

Giri et al., Utilization of the β and γ chains of the IL-2 receptor by the novel cytokine IL-15, *EMBO Journal* 13:2822-2830 (1994).

Grabstein et al., "Cloning of a T Cell Growth Factor That Interacts with the β Chain of the Interleukin-2 Receptor", *Science*, 264:965-968 (1994).

Hatakeyama et al., "A Restricted Cytoplasmic Region of IL-2 Receptor β Chain Is Essential for Growth Signal Transduction but Not for Ligand Binding and Internalization", *Cell*, 59:837-845 (1989).

Isler et al., "Cell surface glycoproteins expressed on activated human T cells induce production of interleukin-1 beta by monocytic cells: a possible role of CD69", *Eur. Cytokine Netw.*, 4:1 15-23, (1993).

Kim et al., Targeting the I1-15 Receptor with an Antagonist IL-15 Mutant/Fcγ2a Protein Blocks Delayed-type Hypersensitivity *Journal of Immunology* 160:5742-5748 (1998).

Kirman and Nielsen, "Increased Number of Interleukin-15-Expressing Cells in Active Ulcerative Colitis", *Am. J. Gastroenterol.*, 91(9):1789-1794, 1996.

Kirman et al., "Interleukin-15 and its role in chronic inflammatory diseases", *Inflamm. Res.*, 47(7):285-289, 1998.

Kivisakk et al., "IL-15 mRNA expression is up-regulated in blood and cerebrospinal fluid mononuclear cells in multiple sclerosis (MS)", *Clin. Exp. Immunol.* 111(1):193-197, 1998.

Knight et al., "Construction and initial characterization of a mouse-human chimeric anti-TNF antibody" *Molecular Immunology* 30:16, 1443-1453 (1993).

LeClair et al., "The p50 subunit of NF-κB associates with the NF-IL6 transcription factor", *Proc. Nat. Acad. Sciences*, 89:8145-8149 (1992).

Li et al., "Differential Expression Of T-cell Growth Factors in Rejecting Murine Islet and Human Renal Allografts", *Transplantation*, 66(2):265-268, 1998.

Lin et al., "The Role of Shared Receptor Motifs and Common Stat Proteins in the Generation of Cytokine Pleiotropy and Redundancy by IL-2, IL-4, IL-7, IL-13 and IL-15", *Immunity*, 2:331-339 (1995).

Liu et al., "IL-15 Is Highly Expressed in Inflammatory Bowel Disease and Regulates Local T Cell-Dependent Cytokine Production", *J. Immunol.* 164(7):3608-3615, 2000.

Maslinski et al., "Interleukin-2 (IL-2) Induces Tyrosine Kinase-dependent Translocation of Active Raf-1 from the IL-2 Receptor into the Cytosol". *J. Biological Chemistry* 267:15281-15284 (1992).

Maslinski et al., "Intoxication of high affinity IL-2 receptor positive thymocytes blocks early stages of T cell maturation", *International Immunology* 4:509-517 (1992).

McInnes and Liew, "Interleukin 15: a proinflammatory role in rheumatoid arthritis synovitis", *Immunol. Today*, 19(2):75-79, 1998.

McInnes et al., "The role of interleukin-15 in T-cell migration and activation in rheumatoid arthritis", *Nature Med.* 2(2):175-182, 1996.

McInnes et al., "Interleukin-15 mediates T cell-dependent regulation of tumor necrosis factor-α production in rheumatoid arthritis", *Nature Med.* 3(2):189-195, 1997.

Mikayama et al. "Molecular cloning and functional expression of a cDNA encoding glycosylation-inhibiting factor", *Proc. Natl. Acad. Sci. USA*, vol. 90, pp. 10056-10060, (1993).

Miltenburg et al., "Immobilized Anti-CD3 Antibody Activates T Cell Clones to Induce the Production of Interstitial Collagenase, but Not Tissue Inhibitor of Metalloproteinases, in Monocytic THP-1 Cells and Dermal Fibroblasts", *The Journal of Immunology*, 154:6 (1995).

Moreland et al., Treatment of Rheumatoid Arthritis with A Recombinant Human Tumor Necrosis Factor Receptor (p75)-Fc Fusion Protein, *NEJM*, 337:3, 141-147 (1997).

Morrison et al., "Structural Determinants of Human IgG Function", *The Immunologist* 2:119-124 (1994).

Nickerson et al., "Prolonged Islet Allograft Acceptance in the Absence of Interleukin 4 Expression", *Transplant Immunology*, 4:81-85 (1996).

Park et al., "Elevated Serum Interleukin-15 Levels in Systemic Lupus Erythematosus", *Yonsei Med. J.* 40(4):343-348, 1999.

Pashenkov et al., "Levels of Interleukin-15-Expressing Blood Mononuclear Cells Are Elevated in Multiple Sclerosis", *Scand. J. Immunol.* 50(3):302-308, 1999.

Pavlakis et al., "Intragraft IL-15 Transcripts Are Increased in Human Renal Allograft Rejection", *Transplantation* 62(4):543-545, 1996.

Pettit et al., "Polyethylene Glycol Conjugation to Lysine Residues of Recombinant IL-15 Generates a Specific IL-15 Antagonist", *Pro. of the Int. Symp. on Cont. Release Bioactive Materials*; 22:496/497 (1995).

Pettit et al., "Structure-Function Studies of Interleukin 15 using Site-specific Mutagenesis, Polyethylene Glycol Conjugation, and Homology Modeling", *J. Biological Chemistry*, 2312-2318 (1997).

Remillard et al., Interleukin-2 Receptor Regulates Activation of Phosphatidylinositol 3-Kinase, *Journal of Biological Chemistry*, 266:14167-14170 (1991).

Rezzonico et al., "Direct Contact between T Lymphocytes and Human Dermal Fibroblasts or Synoviocytes", *Journal of Biological Chemistry* 273:30, 18720-18728 (1998).

Ruchatz et al., "Soluble IL-15 Receptor α-Chain Administration Prevents Murine Collagen-Induced Arthritis: A Role for IL-15 in Development of Antigen-Induced Immunopathology", *J. Immunol.*, 160(11):5654-5660, 1998.

Ruckert et al., "Inhibition of Keratinocyte Apoptosis by IL-15: A New Parameter in the Pathogenesis of Psoriasis", *J. Immunol.* 165(4):2240-2250, 2000.

Sakai et al., "Interleukin 15 Activity in the Rectal Mucosa of Inflammatory Bowel Disease", *Gastroenterology* 114(6):1237-1243, 1998.

Stegall and Krolick, "Myocytes Respond to both Interleukin-4 and Interferon-γ: Cytokine Responsiveness with the Potential to Influence the Severity and Course of Experimental Myasthenia Gravis", *Clin. Immunol.* 94(2):133-139, 2000.

Stevens et al., "Interleukin-15 signals T84 colonic epithelial cells in the absence of the interleukin-2 receptor β chain", *The American Physiological Society* (1997).

Sugiura et al., "Increased CD40 Expression on Muscle Cells of Polymyositis and Dermatomyositis: Role of CD4O-CD40 Ligand Interaction in IL-6, IL-8, IL-15, and Monocyte Chemoattractant Protein-1 Production", *J. Immunol.* 164(12):6593-6600, 2000.

*The Merck Manual of Diagnosis and Therapy. Beers and Berkow. 17th edition*, (1999) pp. 416-430.

Thurkow et al., "Increased Expression of IL-15 in the Synovium of Patients With Rheumatoid Arthritis Compared With Patients With Yersina-Induced Arthritis And Osteoarthritis", *J. Pathol.* 181(4):444-450, 1997.

Tran et al., "IFN-γ Shapes Immune Invasion of the Central Nervous System Via Regulation of Chemokines", *J. Immunol.* 164(5):2759-2768, 2000.

Vey et al., "IFN-γ and 1,25(OH)$_2$ D$_3$ Induce on THP-1 Cells Distinct Patterns of Cell Surface Antigen Expression, Cytokine Production, and Responsiveness to Contact with Activated T Cells", *The Journal of Immunology*, 149:6, 2040-2046 (1992).

Voet et al., *Biochemistry*, John Wiley & Sons, Inc., pp. 126-128 and 228-234, (1990).

Williams et al., "Successful therapy of collagen-induced arthritis with TNF receptor-IgG fusion protein and combination with anit-CD4", *Immunology*, 84:3, 439-439 (1995).

Wooley et al., "Influence of a recombinant human soluble tumor necrosis factor receptor FC fusion protein on type II collagen-induced arthritis in mice", *The Journal of Immunology*, 151:11, 6602-6607 (1993).

Zurawski et al., "Partial agonist/antagonist mouse interleukin-2 proteins indicate that a third component of the receptor complex functions in signal transduction", *EMBO J.*, vol. 9, No. 12 (1990) pp. 3899-3905.

Zuwarski et al., "Definition and spatial location of mouse interleukin-2 residues that interact with its heterotrimeric receptor", *EMBO J.* vol. 12. No. 13 (1993) pp. 5113-5119.

International Search Report dated Oct. 15, 1997 for International Appln. No. PCT/US97/06931 (5 pgs.).

Notice of Reasons for Rejection dated Oct. 17, 2006 for Japanese Appln. No. 9-539046 (with English translation) (14 pgs.).

Partial European Search Report dated Nov. 15, 2005 for European Appln. No. EP 05 01 8287 (6 pgs.).

\* cited by examiner

```
DNA sequence    489 b.p    atgagaatttcg ... aacacttcttga    linear
1/1                                          31/11
atg aga att tcg aaa cca cat ttg aga agt att tcc atc cag tgc tac ttg tgt tta ctt
Met arg ile ser lys pro his leu arg ser ile ser ile gln cys tyr leu cys leu leu
61/21                                        91/31
cta aac agt cat ttt cta act gaa gct ggc att cat gtc ttc att ttg ggc tgt ttc agt
leu asn ser his phe leu thr glu ala gly ile his val phe ile leu gly cys phe ser
121/41                                       151/51
gca ggg ctt cct aaa aca gaa gcc aac tgg gtg aat gta ata agt gat ttg aaa aaa att
ala gly leu pro lys thr glu ala asn trp val asn val ile ser asp leu lys lys ile
181/61                                       211/71
gaa gat ctt att caa tct atg cat att gat gct act tta tat acg gaa agt gat gtt cac
glu asp leu ile gln ser met his ile asp ala thr leu tyr thr glu ser asp val his
241/81                                       271/91
ccc agt tgc aaa gta aca gca atg aag tgc ttt ctc ttg gag tta caa gtt att tca ctt
pro ser cys lys val thr ala met lys cys phe leu leu glu leu gln val ile ser leu
301/101                                      331/111
gag tcc gga gat gca agt att cat gat aca gta gaa aat ctg atc atc ata gca aac aac
glu ser gly asp ala ser ile his asp thr val glu asn leu ile ile ile ala asn asn
361/121                                      391/131
agt ttg tct tct aat ggg aat gta aca gaa tct gga tgc aaa gaa tgt gag gaa ctg gag
ser leu ser ser asn gly asn val thr glu ser gly cys lys glu cys glu glu leu glu
421/141                                      451/151
gaa aaa aat att aaa gaa ttt ttg cag agt ttt gta cat att gtc caa atg ttc atc aac
glu lys asn ile lys glu phe leu gln ser phe val his ile val gln met phe ile asn
481/161
act tct tga
thr ser OPA
```

FIG. 13

DNA sequence    489 b.p.    atgagaatttcg ... aacacttcttga    linear

1/1                                                                              31/11
atg aga att tcg aaa cca cat ttg aga agt att tcc atc cag tgc tac ttg tgt tta ctt
Met arg ile ser lys pro his leu arg ser ile ser ile gln cys tyr leu cys leu leu
61/21                                                                            91/31
cta aac agt cat ttt cta act gaa gct ggc att cat gtc ttc att ttg ggc tgt ttc agt
leu asn ser his phe leu thr glu ala gly ile his val phe ile leu gly cys phe ser
121/41                                                                           151/51
gca ggg ctt cct aaa aca gaa gcc aac tgg gtg aat gta ata agt gat ttg aaa aaa att
ala gly leu pro lys thr glu ala asn trp val asn val ile ser asp leu lys lys ile
181/61                                                                           211/71
gaa gat ctt att caa tct atg cat att gat gct act tta tat acg gaa agt gat gtt cac
glu asp leu ile gln ser met his ile asp ala thr leu tyr thr glu ser asp val his
241/81                                                                           271/91
ccc agt tgc aaa gta aca gca atg aag tgc ttt ctc ttg gag tta caa gtt att tca ctt
pro ser cys lys val thr ala met lys cys phe leu leu glu leu gln val ile ser leu
301/101                                                                          331/111
gag tcc gga gat gca agt att cat gat aca gaa aat ctg atc atc ile leu ala asn asn
glu ser gly asp ala ser ile his asp thr glu asn leu ile ile leu ala asn asn
361/121                                                                          391/131
agt ttg tct tct aat ggg aat gta aca gaa tct gga tgc aaa gaa tgt gag gaa ctg gag
ser leu ser ser asn gly asn val thr glu ser gly cys lys glu cys glu glu leu glu
421/141                                                                          451/151
gaa aaa aat att aaa gaa att gta cat ttt ttg gac agt ttt gta cat gtc gac atg ttc atc aac
glu lys asn ile lys glu ile val his phe leu asp ser phe val his ile val asp met phe ile asn
481/161
act tct tga
thr ser OPA

FIG. 14

M1=8.8% of gated events
M1=32.6% of gated events

SEQUENCE LISTING

<160> NUMBER OF SEQ ID NOS: 12

<210> SEQ ID NO 1
<211> LENGTH: 25
<212> TYPE: DNA
<213> ORGANISM: Artificial Sequence
<220> FEATURE:
<223> OTHER INFORMATION: synthetically generated primer

<400> SEQUENCE: 1
ggaattcaac tgggtgaatg taata                                         25

<210> SEQ ID NO 2
<211> LENGTH: 26
<212> TYPE: DNA
<213> ORGANISM: Artificial Sequence
<220> FEATURE:

<210> SEQ ID NO 2
<211> LENGTH: 26
<212> TYPE: DNA
<213> ORGANISM: Artificial Sequence
<220> FEATURE:
<223> OTHER INFORMATION: synthetically generated primer

<400> SEQUENCE: 2
cgggatcctc aagaagtgtt gatgaa                                              26

<210> SEQ ID NO 3
<211> LENGTH: 60
<212> TYPE: DNA
<213> ORGANISM: Artificial Sequence
<220> FEATURE:
<223> OTHER INFORMATION: synthetically generated primer

<400> SEQUENCE: 3
cgggatcctc aagaagtgtt gatgaacatg tcgacaatat gtacaaaact gtccaaaaat        60

<210> SEQ ID NO 4
<211> LENGTH: 7
<212> TYPE: PRT
<213> ORGANISM: Artificial Sequence
<220> FEATURE:
<223> OTHER INFORMATION: synthetically generated peptide

<400> SEQUENCE: 4

Asp Tyr Lys Asp Asp Asp Lys
 1               5

<210> SEQ ID NO 5
<211> LENGTH: 489
<212> TYPE: DNA
<213> ORGANISM: Homo sapiens
<220> FEATURE:
<221> NAME/KEY: CDS
<222> LOCATION: (1)...(486)

<400> SEQUENCE: 5

```
atg aga att tcg aaa cca cat ttg aga agt att tcc atc cag tgc tac        48
Met Arg Ile Ser Lys Pro His Leu Arg Ser Ile Ser Ile Gln Cys Tyr
 1               5                  10                  15 ttg tgt tta ctt cta aac agt cat ttt cta act gaa gct ggc att cat        96
Leu Cys Leu Leu Leu Asn Ser His Phe Leu Thr Glu Ala Gly Ile His
             20                  25                  30 gtc ttc att ttg ggc tgt ttc agt gca ggg ctt cct aaa aca gaa gcc       144
Val Phe Ile Leu Gly Cys Phe Ser Ala Gly Leu Pro Lys Thr Glu Ala
         35                  40                  45 aac tgg gtg aat gta ata agt gat ttg aaa aaa att gaa gat ctt att       192
Asn Trp Val Asn Val Ile Ser Asp Leu Lys Lys Ile Glu Asp Leu Ile
     50                  55                  60 caa tct atg cat att gat gct act tta tat acg gaa agt gat gtt cac       240
Gln Ser Met His Ile Asp Ala Thr Leu Tyr Thr Glu Ser Asp Val His
 65                  70                  75                  80 ccc agt tgc aaa gta aca gca atg aag tgc ttt ctc ttg gag tta caa       288
Pro Ser Cys Lys Val Thr Ala Met Lys Cys Phe Leu Leu Glu Leu Gln
                 85                  90                  95 gtt att tca ctt gag tcc gga gat gca agt att cat gat aca gta gaa       336
Val Ile Ser Leu Glu Ser Gly Asp Ala Ser Ile His Asp Thr Val Glu
            100                 105                 110 aat ctg atc atc cta gca aac aac agt ttg tct tct aac ggg aat gta       384
Asn Leu Ile Ile Leu Ala Asn Asn Ser Leu Ser Ser Asn Gly Asn Val
        115                 120                 125 aca gaa tct gga tgc aaa gaa tgt gag gaa ctg gag gaa aaa aat att       432
Thr Glu Ser Gly Cys Lys Glu Cys Glu Glu Leu Glu Glu Lys Asn Ile
    130                 135                 140 aaa gaa ttt ttg cag agt ttt gta cat att gtc caa atg ttc atc aac       480
Lys Glu Phe Leu Gln Ser Phe Val His Ile Val Gln Met Phe Ile Asn
145                 150                 155                 160
```

```
Lys Glu Phe Leu Gln Ser Phe Val His Ile Val Gln Met Phe Ile Asn
145                 150                 155                 160 act tct tga                                                                    489
Thr Ser <210> SEQ ID NO 6
<211> LENGTH: 162
<212> TYPE: PRT
<213> ORGANISM: Homo sapiens

<400> SEQUENCE: 6

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
                20                  25                  30

Val Phe Ile Leu Gly Cys Phe Ser Ala Gly Leu Pro Lys Thr Glu Ala
            35                  40                  45

Asn Trp Val Asn Val Ile Ser Asp Leu Lys Lys Ile Glu Asp Leu Ile
        50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
130                 135                 140

Lys Glu Phe Leu Gln Ser Phe Val His Ile Val Gln Met Phe Ile Asn
145                 150                 155                 160

Thr Ser

<210> SEQ ID NO 7
<211> LENGTH: 489
<212> TYPE: DNA
<213> ORGANISM: Artificial Sequence
<220> FEATURE:
<223> OTHER INFORMATION: synthetically generated nucleic acid sequence
<220> FEATURE:
<221> NAME/KEY: CDS
<222> LOCATION: (1)...(486)

<400> SEQUENCE: 7 atg aga att tcg aaa cca cat ttg aga agt att tcc atc cag tgc tac         48
Met Arg Ile Ser Lys Pro His Leu Arg Ser Ile Ser Ile Gln Cys Tyr
1               5                   10                  15 ttg tgt tta ctt cta aac agt cat ttt cta act gaa gct ggc att cat         96
Leu Cys Leu Leu Leu Asn Ser His Phe Leu Thr Glu Ala Gly Ile His
                20                  25                  30 gtc ttc att ttg ggc tgt ttc agt gca ggg ctt cct aaa aca gaa gcc        144
Val Phe Ile Leu Gly Cys Phe Ser Ala Gly Leu Pro Lys Thr Glu Ala
            35                  40                  45 aac tgg gtg aat gta ata agt gat ttg aaa aaa att gaa gat ctt att        192
Asn Trp Val Asn Val Ile Ser Asp Leu Lys Lys Ile Glu Asp Leu Ile
        50                  55                  60 caa tct atg cat att gat gct act tta tat acg gaa agt gat gtt cac        240
Gln Ser Met His Ile Asp Ala Thr Leu Tyr Thr Glu Ser Asp Val His
65                  70                  75                  80
```

```
ccc agt tgc aaa gta aca gca atg aag tgc ttt ctc ttg gag tta caa    288
Pro Ser Cys Lys Val Thr Ala Met Lys Cys Phe Leu Leu Glu Leu Gln
            85                  90                  95 gtt att tca ctt gag tcc gga gat gca agt att cat gat aca gta gaa    336
Val Ile Ser Leu Glu Ser Gly Asp Ala Ser Ile His Asp Thr Val Glu
       100                 105                 110 aat ctg atc atc cta gca aac aac agt ttg tct tct aac ggg aat gta    384
Asn Leu Ile Ile Leu Ala Asn Asn Ser Leu Ser Ser Asn Gly Asn Val
           115                 120                 125 aca gaa tct gga tgc aaa gaa tgt gag gaa ctg gag gaa aaa aat att    432
Thr Glu Ser Gly Cys Lys Glu Cys Glu Glu Leu Glu Glu Lys Asn Ile
       130                 135                 140 aaa gaa ttt ttg gac agt ttt gta cat att gtc gac atg ttc atc aac    480
Lys Glu Phe Leu Asp Ser Phe Val His Ile Val Asp Met Phe Ile Asn
145                 150                 155                 160 act tct tga                                                        489
Thr Ser
```

<210> SEQ ID NO 8
<211> LENGTH: 162
<212> TYPE: PRT
<213> ORGANISM: Artificial Sequence
<220> FEATURE:
<223> OTHER INFORMATION: synthetically generated protein

<400> SEQUENCE: 8

```
Met Arg Ile Ser Lys Pro His Leu Arg Ser Ile Ser Ile Gln Cys Tyr
 1               5                  10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

Asn Trp Val Asn Val Ile Ser Asp Leu Lys Lys Ile Glu Asp Leu Ile
 50                  55                  60

Gln Ser Met His Ile Asp Ala Thr Leu Tyr Thr Glu Ser Asp Val His
 65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
           100                 105                 110

Asn Leu Ile Ile Leu Ala Asn Asn Ser Leu Ser Ser Asn Gly Asn Val
            115                 120                 125

Thr Glu Ser Gly Cys Lys Glu Cys Glu Glu Leu Glu Glu Lys Asn Ile
        130                 135                 140

Lys Glu Phe Leu Asp Ser Phe Val His Ile Val Asp Met Phe Ile Asn
145                 150                 155                 160

Thr Ser
```

<210> SEQ ID NO 9
<211> LENGTH: 23
<212> TYPE: DNA
<213> ORGANISM: Artificial Sequence
<220> FEATURE:
<223> OTHER INFORMATION: synthetically generated primer

<400> SEQUENCE: 9
ccaacggcat ggatctcaaa gac                                          23

<210> SEQ ID NO 10

-continued

```
<211> LENGTH: 25
<212> TYPE: DNA
<213> ORGANISM: Artificial Sequence
<220> FEATURE:
<223> OTHER INFORMATION: synthetically generated primer

<400> SEQUENCE: 10
tcactgtccc agcatcttgt gtttc                                              25

<210> SEQ ID NO 11
<211> LENGTH: 24
<212> TYPE: DNA
<213> ORGANISM: Artificial Sequence
<220> FEATURE:
<223> OTHER INFORMATION: synthetically generated primer

<400> SEQUENCE: 11
tgcactacag gctccgagat gaac                                               24

<210> SEQ ID NO 12
<211> LENGTH: 25
<212> TYPE: DNA
<213> ORGANISM: Artificial Sequence
<220> FEATURE:
<223> OTHER INFORMATION: synthetically generated primer

<400> SEQUENCE: 12
catcagaggc aaggaggaaa cacag                                              25
```

ANTAGONISTS OF INTERLEUKIN-15

RELATED APPLICATIONS

This application is a continuation of U.S. Ser. No. 10/245,243, filed Sep. 17, 2002, now U.S. Pat. No. 7,258,853 which is a continuation of U.S. Ser. No. 09/437,585, filed Nov. 9, 1999, now U.S. Pat. No. 6,451,308, which is a continuation-in-part of U.S. Ser. No. 08/842,947, filed Apr. 25, 1997, now U.S. Pat. No. 6,001,973, which claims benefit from U.S. Ser. No. 60/016,634, filed Apr. 26, 1996.

FIELD OF THE INVENTION

The field of the invention is cytokine-mediated therapeutics.

BACKGROUND OF THE INVENTION

An effective immune response begins when an antigen or mitogen triggers the activation of T cells. In the process of T cell activation, numerous cellular changes occur, which include the expression of cytokines and cytokine receptors. One of the cytokines involved in the immune response is interleukin-15 (IL-15). IL-15 is a T cell growth factor that stimulates the proliferation and differentiation of B cells, T cells, natural killer (NK) cells, and lymphocyte-activated killer (LAK) cells in vitro. In vivo, the proliferation of these cell types enhances the immune response.

IL-15 binds to a heterotrimeric receptor that consists of the IL-2Rβ subunit, the IL-2Rγ subunit, and a unique IL-15Rα subunit.

Patients benefit from suppression of the immune response in a number of circumstances, for example, in the event of organ transplantation or autoimmune disease. In other circumstances, for example when select immune cells have become malignant or autoaggressive, it is beneficial to actively destroy them.

SUMMARY OF THE INVENTION

The invention features mutants of the cytokine IL-15. Preferably, these mutants bind the IL-15 receptor complex with an affinity similar to wild-type IL-15, but fail to activate signal transduction. The mutant polypeptides of the invention therefore compete effectively with wild-type IL-15 and, when they do so, they block one or more of the events that normally occur in response to IL-15 signalling, such as cellular proliferation. By modulating the events mediated by the IL-15 receptor complex, mutant IL-15 polypeptides can modulate the immune response, and thus are therapeutically useful.

Mutant IL-15 polypeptides can have several characteristics that are advantageous in the context of treatment regimes. First, they are unlikely to be immunogenic because they can differ from wild type IL-15 by only a few substituted residues.

Second, IL-15 mutants can bind IL-15Rα with the same high affinity as wild type IL-15 and thus, can compete effectively for the receptor. Third, IL-15 mutants can be easily modified to remain active in the circulation for a prolonged period of time, or to produce a lytic response in cells to which they bind. In addition, the IL-15 receptor alpha IL-15Rα polypeptide is expressed by activated or malignant immune cells, but not on resting immune cells. Thus, the mutant polypeptide of the invention can be used to specifically target activated or malignant immune cells.

Other features and advantages of the invention will be apparent from the following detailed description, and from the claims. Although materials and methods similar or equivalent to those described herein can be used in the practice or testing of the invention, the preferred materials and methods are described below.

BRIEF DESCRIPTION OF THE DRAWINGS

FIG. 5A demonstrates the existence of IL-2Rα+ cells that do not bind FLAG-HMK-IL-15. FIG. 5B demonstrates that almost all PBMCs stimulated with PHA for only one day express either IL-15Rα or IL-2Rβ subunits, but not both. FIG. 5C demonstrates that a larger population of IL-15Rα+ and IL-2Rβ+ cells (double positive) are present 3 days following PHA stimulation.

FIG. 6B), rapamycin (RAPA; FIG. 6C), or dexamethasone (Dex; FIG. 6D) for 20 minutes before the addition of PHA and then cultured for 3 days. The control, stimulation with PHA only, is shown in FIG. 6A. The level of IL-15Rα expression was detected using FLAG-HMK-IL-15, anti-FLAG biotinylated Ab, streptavidin-RED670, and FACS analysis.

FIG. 13 is a representation of the wild-type IL-15 nucleic acid and predicted amino acid sequence.

FIG. 14 is a representation of the mutant IL-15 nucleic acid and predicted amino acid sequence. The wild-type codon encoding glutamine at position 149[1], CAG, and the wild-type codon encoding glutamine at position 156, CAA, have both been changed to GAC, which encodes aspartate. (These positions (149 and 156) correspond to positions 101 and 108, respectively, in the mature IL-15 polypeptide, which lacks a 48-amino acid signal sequence).

[1] In the provisional application from which the instant application ultimately claims benefit (U.S. Ser. No. 60/016,634), the residues circled on FIGS. 14 and 15 (which are now shown as FIGS. 13 and 14, respectively) were counted incorrectly and identified as residues 169 and 176. These residues are, in fact, at positions 149 and 156. Accordingly, all references to positions 169 and 176 in the provisional application have been changed herein to positions 149 and 156, respectively.

Figure 15:
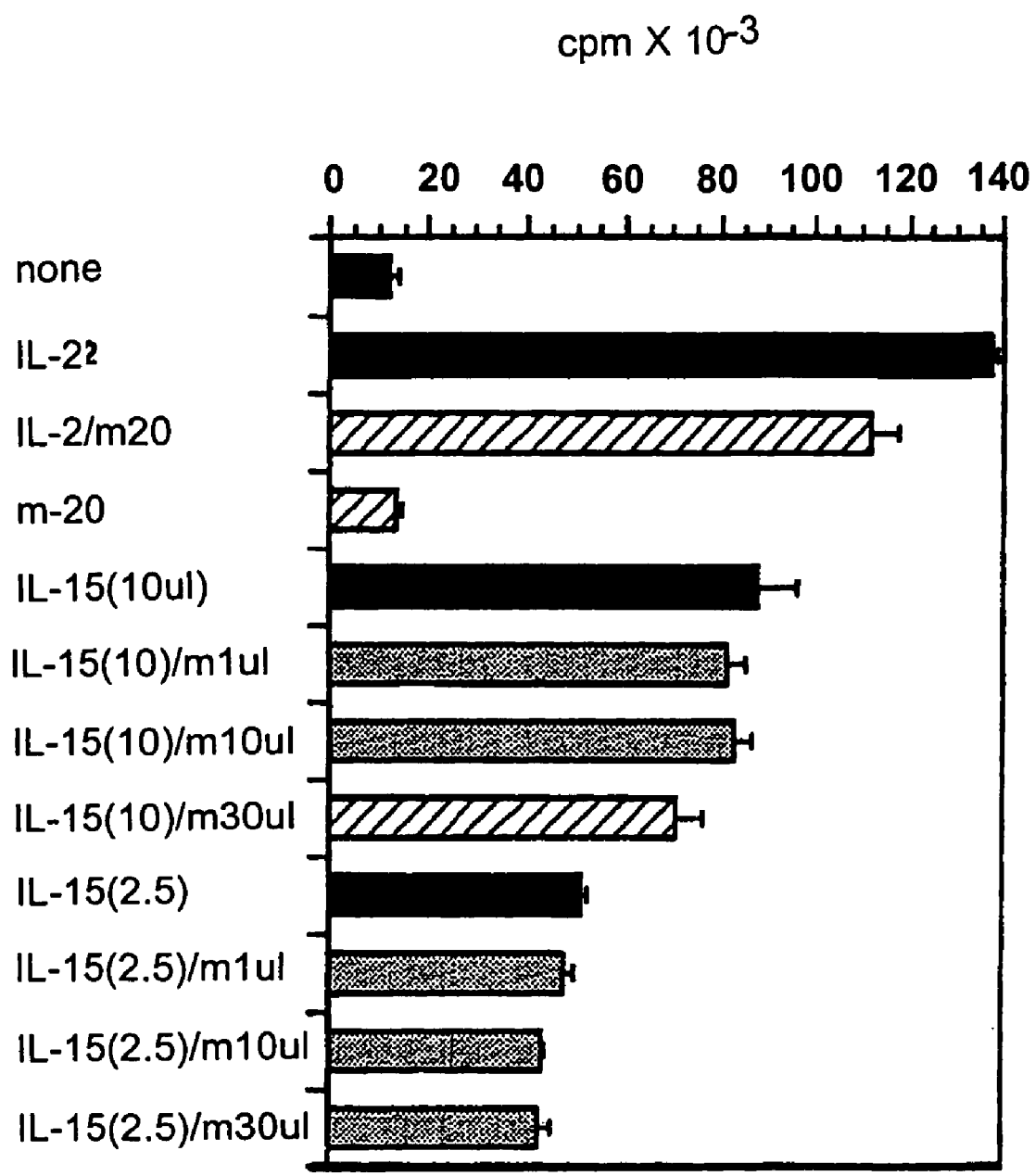

FIG. 15 is a bar graph depicting the proliferative response of BAF-BO3 cells cultured in the presence of IL-15 related polypeptides. Abbreviations: WT=BAF-BO3 cells transfected with Prccmv-IL-2Rβ (encoding the human IL-2Rβ subunit); V=BAF-BO3 cells transfected with Prccmv-0 (plasmid without insert); none=incubation of cells in medium without added interleukin; DM=incubation of cells in medium containing the IL-15 double mutant (FLAG-HMK-IL-15-Q149D-Q156D); 149=incubation of cells in medium containing the IL-15 single mutant (FLAG-HMK-IL-15-Q149D).

Figure 16:
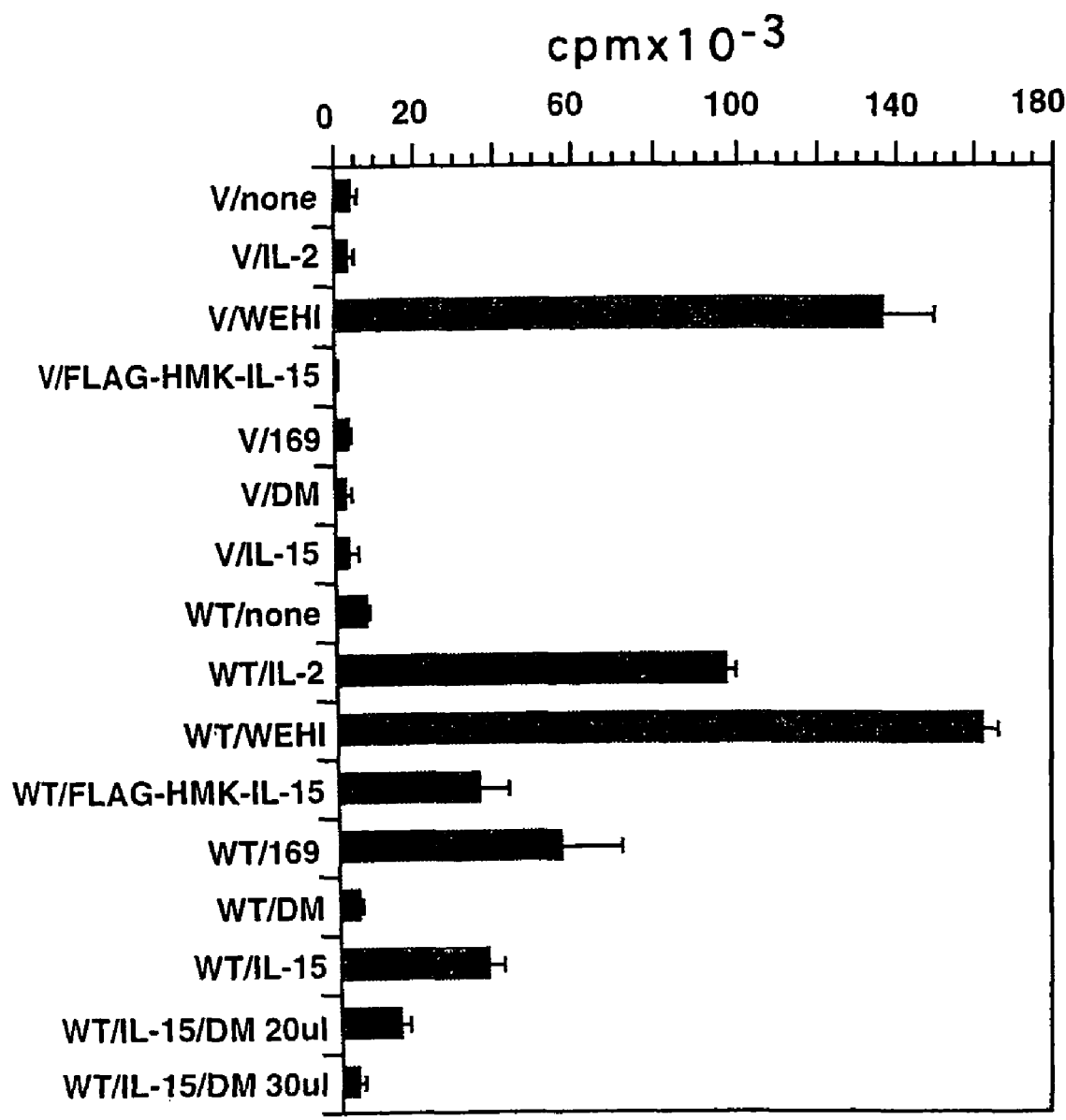

FIG. 16 is a bar graph depicting the proliferative response of PHA-stimulated human PBMCs cultured in the presence of IL-15 related proteins. Abbreviations: WT=BAF-BO3 cells transfected with Prccmv-IL-2Rβ (encoding the human IL-2Rβ subunit); V=BAF-BO3 cells transfected with Prccmv-0 (plasmid without insert); none=incubation of cells in medium without added interleukin; DM=incubation of cells in medium containing the IL-15 double mutant (FLAG-HMK-IL-15-Q149D-Q156D); 149=incubation of cells in medium containing the IL-15 single mutant (FLAG-HMK-IL-15-Q149D); 156=incubation of cells in medium containing the IL-15 single mutant (FLAG-HMK-IL-15-Q156D).

Figure 17A:
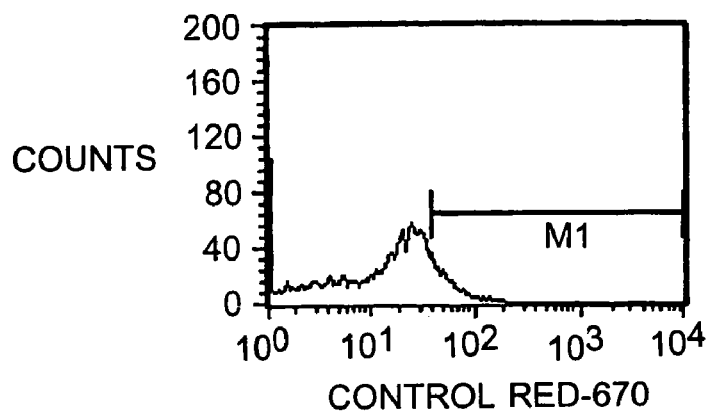
Figure 17B:
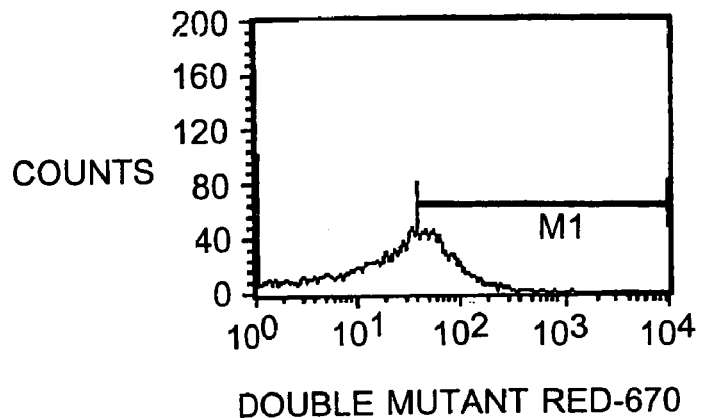
Figure 17C:
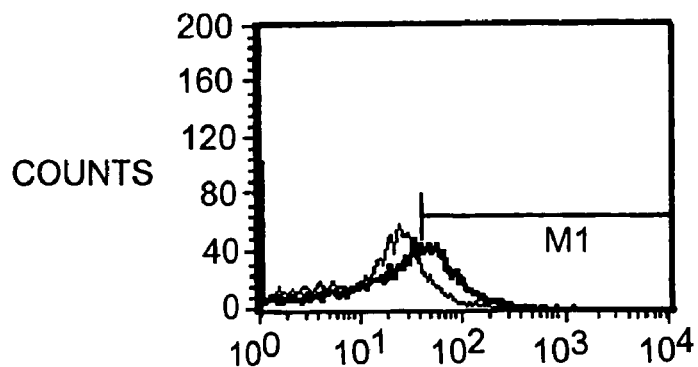

FIGS. 17A through 17C are a series of plots demonstrating the ability of the FLAG-HMK-IL-15 double mutant to bind PHA-activated human PBMCs. PHA-activated PBMCs were washed and incubated with medium alone (FIG. 17A) or with FLAG-HMK-IL-15 double mutant (FIG. 17B) followed by anti-FLAG biotinylated Ab and streptavidin-RED670. The stained cells were analyzed by flow cytometry. In (FIGS. 17A-17C), show overlapped control and mutant lines (control=thin line; FLAG-HMK-IL-15-double mutant=thick line).

Figure 18A:
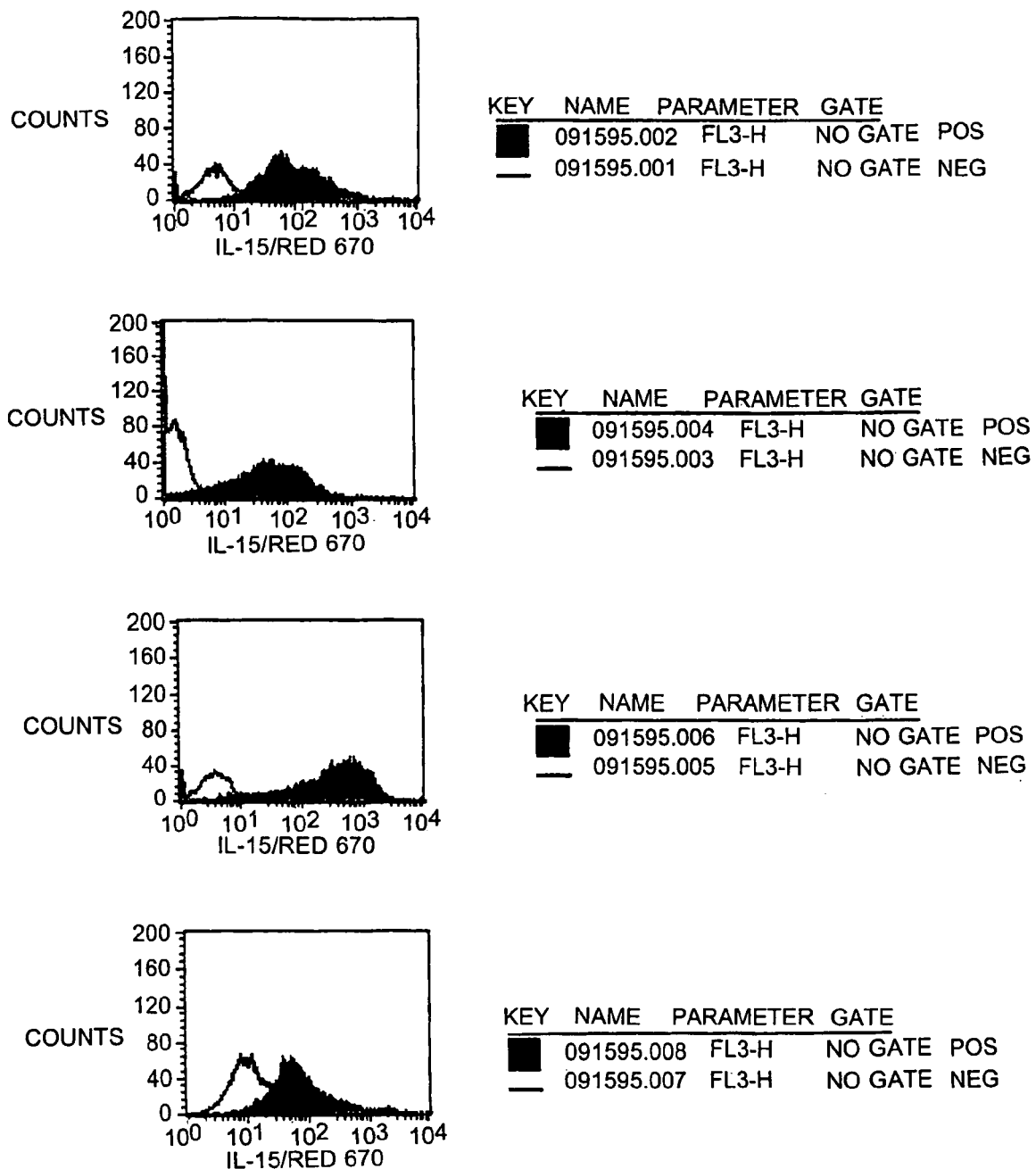
Figure 18B:
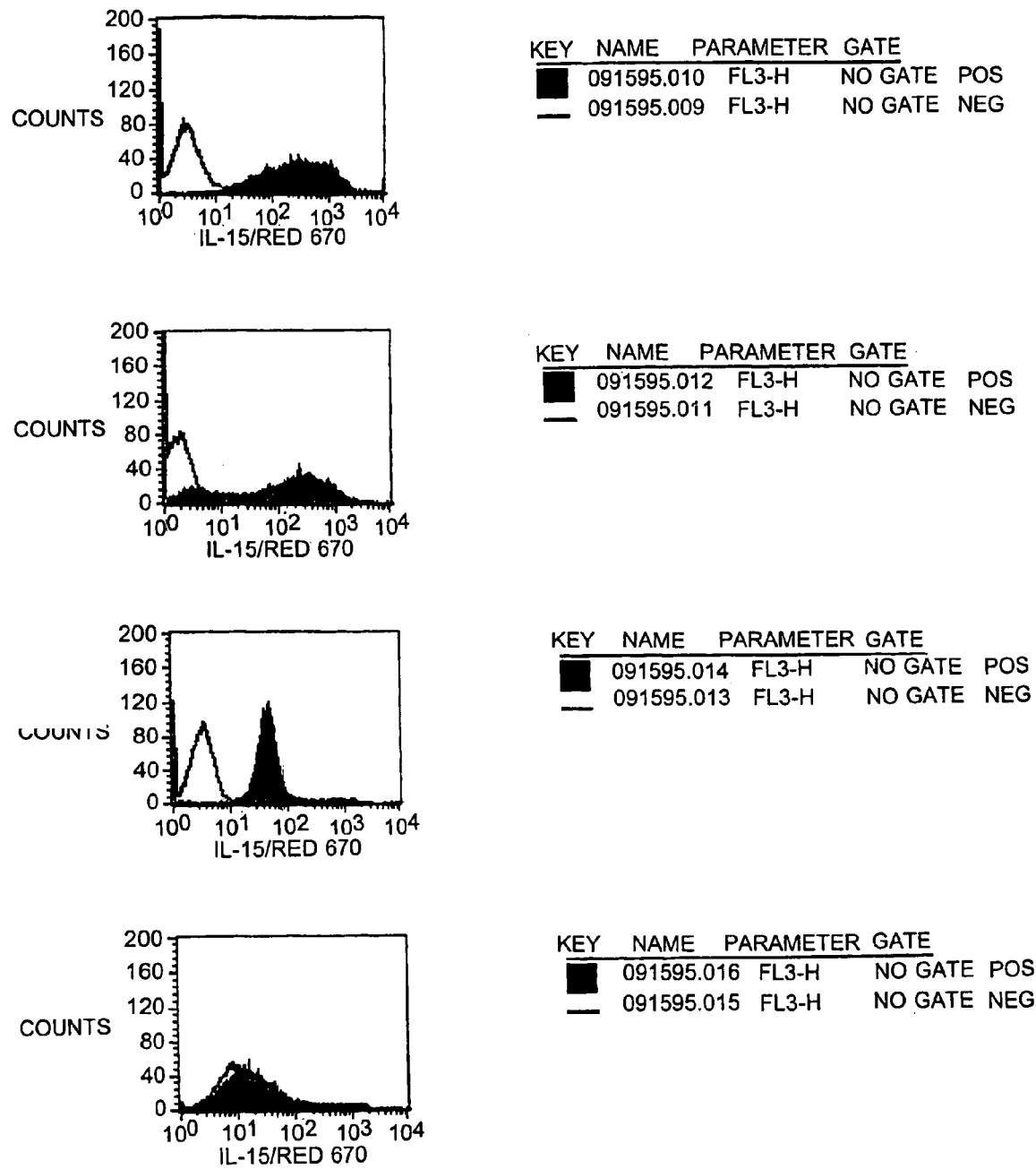

FIGS. 18A and 18B are a series of plots demonstrating the ability of the wild-type FLAG-HMK-IL-15 polypeptide to bind leukemia cells. The cells treated were from the leukemic cell lines MOLT-14, YT, HuT-102, and from cell lines currently being established at Beth Israel Hospital (Boston, Mass.), and designated 2A and 2B. The cultured cells were washed and incubated with either medium alone (tracing alone) or with medium containing the FLAG-HMK-IL-15 polypeptide (tracing filled in). The cells were then incubated with the biotinylated anti-FLAG antibody and stained with RED670-conjugated streptavidin. The stained cells were analyzed by flow cytometry.

Figure 19A:
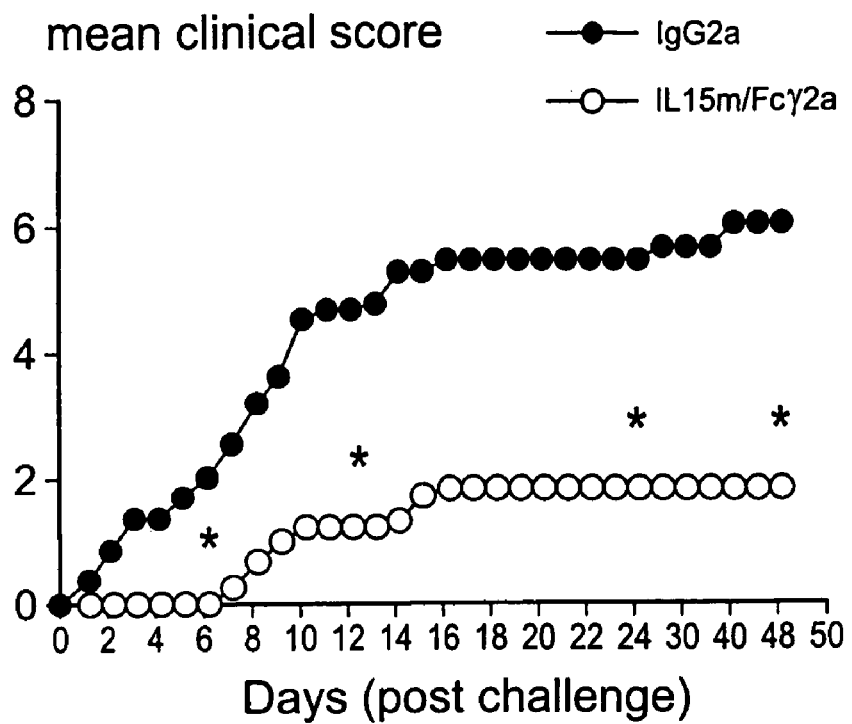
Figure 19B:
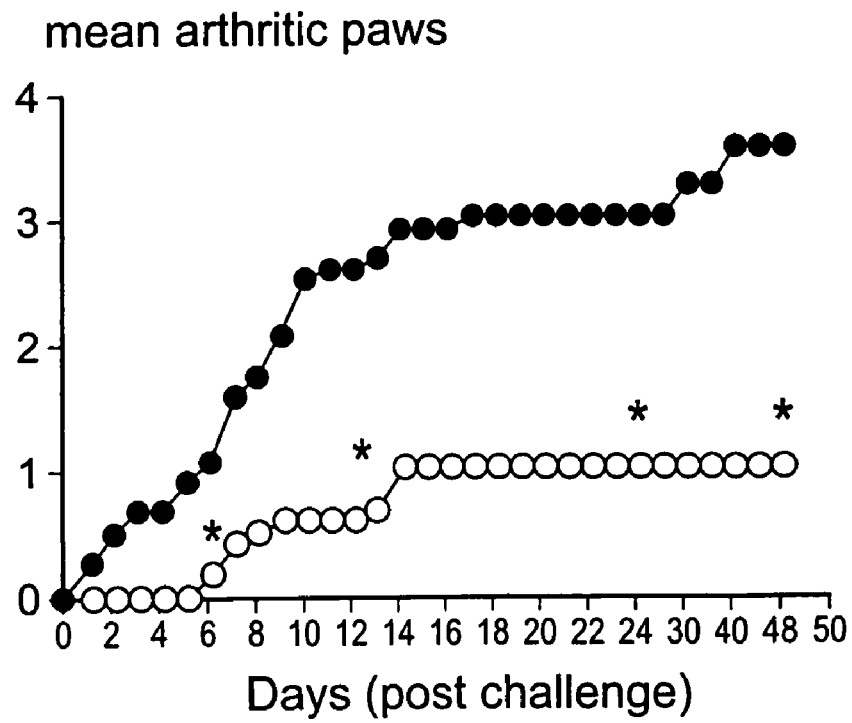

FIGS. 19A and 19B are graphs depicting the effects of a mutant IL-15/Fcγ2a polypeptide on the development of CIA in DBA/1 mice. Administration of the polypeptide delays the onset and decreases the incidence of CIA. Mice were immunized with intradermal injection of CII and rechallenged with CII 21 days later. On the day of challenge, mice were randomly divided into two groups, one receiving daily intraperitoneal injections of control IgG2a (1.5 μg/mouse (●) or mutant IL-15/Fcγ2a (1.5 μg/mouse) (○). Mice were examined every day for disease activity, which was quantified as mean clinical score (FIG. 19A) or mean number of arthritic paws (FIG. 19B).

DETAILED DESCRIPTION

Mutant IL-15 polypeptides can suppress IL-15 dependent immune responses by selectively inhibiting the activity of cells that bind wild-type IL-15. The mutant can also be used to kill the cells to which it binds.

Accordingly, the invention features a substantially pure polypeptide that is a mutant of wild-type IL-15, nucleic acid molecules that encode this polypeptide, and cells that express the mutant polypeptide. Methods of treatment, wherein a mutant IL-15 polypeptide is administered to suppress the immune response (for example, in the event of an autoimmune disease) or to kill IL-15-binding cells (for example, in the event of unwanted cellular proliferation of IL-15-binding cells) are also within the scope of the invention.

Mutant IL-15 Polypeptides

The invention features a substantially pure polypeptide that is a mutant of wild-type IL-15, and which can function as an antagonist of wild-type IL-15. The "wild-type IL-15 polypeptide" referred to herein is a polypeptide that is identical to a naturally-occurring IL-15 (interleukin-15) polypeptide. IL-15 has been characterized as a T cell growth factor that stimulates the proliferation and differentiation of B cells, T cells, natural killer (NK) cells, and lymphocyte-activated killer (LAK) cells in vitro. In contrast, a "mutant IL-15 polypeptide" is a polypeptide that has at least one mutation relative to wild-type IL-15 and that inhibits any in vivo or in vitro activity that is characteristic of wild-type IL-15.

A mutant IL-15 polypeptide that can be used according to the present invention will generally blocks at least 40%, more preferably at least 70%, and most preferably at least 90% of one or more of the activities of the wild-type IL-15 molecule. The ability of a mutant IL-15 polypeptide to block wild-type IL-15 activity can be assessed by numerous assays, including the BAF-BO3 cell proliferation assay described herein (in which the cells were transfected with a construct encoding IL-2Rβ).

The mutant polypeptides of the invention can be referred to as exhibiting a particular percent identity to wild-type IL-15. When examining the percent identity between two polypeptides, the length of the sequences compared will generally be at least 16 amino acids, preferably at least 20 amino acids, more preferably at least 25 amino acids, and most preferably at least 35 amino acids.

The term "identity," as used herein in reference to polypeptide or DNA sequences, refers to the subunit sequence identity between two molecules. When a subunit position in both of the molecules is occupied by the same monomeric subunit (i.e., the same amino acid residue or nucleotide), then the molecules are identical at that position. The similarity between two amino acid or two nucleotide sequences is a direct function of the number of identical positions. Thus, a polypeptide that is 50% identical to a reference polypeptide that is 100 amino acids long can be a 50 amino acid polypeptide that is completely identical to a 50 amino acid long portion of the reference polypeptide. It might also be a 100 amino acid long polypeptide that is 50% identical to the reference polypeptide over its entire length. Of course, many other polypeptides will meet the same criteria.

Sequence identity is typically measured using sequence analysis software such as the Sequence Analysis Software Package of the Genetics Computer Group at the University of Wisconsin Biotechnology Center (1710 University Avenue, Madison, Wis. 53705), with the default parameters thereof.

The mutant polypeptide can be at least 65%, preferably at least 80%, more preferably at least 90%, and most preferably at least 95% (e.g., 99%) identical to wild-type IL-15. The mutation can consist of a change in the number or content of amino acid residues. For example, the mutant IL-15 can have a greater or a lesser number of amino acid residues than wild-type IL-15. Alternatively, or in addition, the mutant polypeptide can contain a substitution of one or more amino acid residues that are present in the wild-type IL-15. The mutant IL-15 polypeptide can differ from wild-type IL-15 by the addition, deletion, or substitution of a single amino acid residue, for example, a substitution of the residue at position 156. Similarly, the mutant polypeptide can differ from wild-type by a substitution of two amino acid residues, for example, the residues at positions 156 and 149. For example, the mutant IL-15 polypeptide can differ from wild-type IL-15 by the substitution of aspartate for glutamine at residues 156 and 149 (as shown in FIGS. 14 and 15). Additions, deletions, and substitutions of more than two residues, and substitutions at other positions are likely to produce a similarly useful (i.e., therapeutically effective) mutant IL-15 polypeptide.

The substituted amino acid residue(s) can be, but are not necessarily, conservative substitutions, which typically include substitutions within the following groups: glycine, alanine; valine, isoleucine, leucine; aspartic acid, glutamic acid; asparagine, glutamine; serine, threonine; lysine, arginine; and phenylalanine, tyrosine.

The mutations described above can be in the carboxy-terminal domain of the cytokine, which is believed to bind the IL-2Rγ subunit. It is also possible that one or more mutations can be within the IL-2Rβ binding domain.

In a related aspect, the invention features a chimeric polypeptide that includes a mutant IL-15 polypeptide and a heterologous polypeptide (i.e., a polypeptide that is not IL-15 or a mutant thereof). The heterologous polypeptide can increase the circulating half-life of the chimeric polypeptide in vivo. The polypeptide that increases the circulating half-life may be a serum albumin, such as human serum albumin, or the Fc region of the IgG subclass of antibodies that lacks the IgG heavy chain variable region. The Fc region may include a mutation that inhibits complement fixation and Fc receptor binding, or it may be lytic, i.e., able to bind complement or to lyse cells via another mechanism, such as antibody-dependent complement lysis (ADCC; Ser. No. 08/355,502 filed Dec. 12, 1994).

The "Fc region" can be a naturally-occurring or synthetic polypeptide that is homologous to the IgG C-terminal domain produced by digestion of IgG with papain. IgG Fc has a molecular weight of approximately 50 Kda. The polypeptides of the invention can include the entire Fc region, or a smaller portion that retains the ability to extend the circulating half-life of a chimeric polypeptide of which it is a part. In addition, full-length or fragmented Fc regions can be variants of the wild-type molecule. This is, they can contain mutations that may or may not affect the function of the polypeptide; as described further below, native activity is not necessary or desired in all cases.

The Fc region can be "lytic" or "non-lytic." A non-lytic Fc region typically lacks a high affinity Fc receptor binding site and a C'1q binding site. The high affinity Fc receptor binding site of murine IgG Fc includes the Leu residue at position 235 of IgG Fc. Thus, the Fc receptor binding site can be destroyed by mutating or deleting Leu 235. For example, substitution of Glu for Leu 235 inhibits the ability of the Fc region to bind the high affinity Fc receptor. The murine C'1q binding site can be functionally destroyed by mutating or deleting the Glu 318, Lys 320, and Lys 322 residues of IgG. For example, substitution of Ala residues for Glu 318, Lys 320, and Lys 322 renders IgG1 Fc unable to direct antibody-dependent complement lysis. In contrast, a lytic IgG Fc region has a high affinity Fc receptor binding site and a C'1q binding site. The high affinity Fc receptor binding site includes the Leu residue at position 235 of IgG Fc, and the C'1q binding site includes the Glu 318, Lys 320, and Lys 322 residues of IgG1. Lytic IgG Fc has wild-type residues or conservative amino acid substitutions at these sites. Lytic IgG Fc can target cells for antibody dependent cellular cytotoxicity or complement directed cytolysis (CDC). Appropriate mutations for human IgG are also known (see, e.g., Morrison et al., *The Immunologist* 2:119-124, 1994; and Brekke et al., *The Immunologist* 2:125, 1994).

In other instances, the chimeric polypeptide may include the mutant IL-15 polypeptide and a polypeptide that functions as an antigenic tag, such as a FLAG sequence. FLAG sequences are recognized by biotinylated, highly specific, anti-FLAG antibodies, as described herein (see also Blanar et al., *Science* 256:1014, 1992; LeClair et al., *Proc. Natl. Acad. Sci. USA* 89:8145, 1992).

Chimeric polypeptides can be constructed using no more than conventional molecular biological techniques, which are well within the ability of those of ordinary skill in the art to perform.

As used herein, the terms "protein," "peptide" and "polypeptide" refer to any chain of amino acid residues, regardless of length or post-translational modification (e.g., glycosylation or phosphorylation). The proteins or polypeptides of the invention are "substantially pure," meaning that they are at least 60% by weight (dry weight) the polypeptide of interest, for example, a polypeptide containing the mutant IL-15 amino acid sequence. Preferably, the polypeptide is at least 75%, more preferably at least 90%, and most preferably at least 99%, by weight, the polypeptide of interest. Purity can be measured by any appropriate standard method, for example, column chromatography, polyacrylamide gel electrophoresis, or HPLC analysis.

In general, the polypeptides used in the practice of the instant invention will be synthetic, or produced by expression of a recombinant nucleic acid molecule. Polypeptides that are derived from eukaryotic organisms or synthesized in *E. coli*, or is other prokaryotes, and polypeptides that are chemically synthesized will be substantially free from some or all of their naturally associated components. In the event the polypeptide is a chimera, it can be encoded by a hybrid nucleic acid molecule (such as those discussed further below) containing one sequence that encodes all or part of the mutant IL-15, and a second sequence that encodes all or part of a second gene. For example, the mutant IL-15 polypeptide may be fused to a hexa-histidine tag to facilitate purification of bacterially expressed protein, or to a hemagglutinin tag to facilitate purification of protein expressed in eukaryotic cells.

The techniques that are required to make mutant IL-15 polypeptides are routine in the art, and can be performed without resort to undue experimentation by artisans of ordinary skill. For example, a mutation that consists of a substitution of one or more of the amino acid residues in IL-15 can be created using the PCR-assisted mutagenesis technique described herein for the creation of mutant IL-15 polypeptides. As one non-limiting example, glutamine residues at positions 149 and 156 can be changed as described below to aspartic acid residues. Mutations that consists of deletions or additions of amino acid residues to an IL-15 polypeptide can also be made with standard recombinant techniques. In the event of a deletion or addition, the nucleic acid molecule encoding IL-15 is simply digested with an appropriate restriction endonuclease. The resulting fragment can either be expressed directly, or manipulated further, for example, by ligating it to a second fragment. The ligation may be facilitated if the two ends of the nucleic acid molecules contain complementary nucleotides that overlap one another, but blunt-ended fragments can also be ligated.

In addition to generating mutant polypeptides via expression of nucleic acid molecules that have been altered by recombinant molecular biological techniques, mutant polypeptides can be chemically synthesized. Chemically synthesized polypeptides are routinely generated by those of skill in the art.

Procedures for Screening Mutant IL-15 Polypeptides

Candidate mutants made, for example, as described above can be screened for the requisite activity. In addition to testing a candidate mutant IL-15 polypeptide in the in vitro assays described in the examples below, the following procedures can be employed to determine whether a mutant IL-15 polypeptide is capable of functioning as an antagonist of IL-15 in vivo.

Transplantation Paradigms

In order to determine whether a polypeptide is capable of functioning as an immunosuppressant, it can be administered, either directly or by genetic therapy, in the context of well-established transplantation paradigms.

A putative immunosuppressive polypeptide, or a nucleic acid molecule encoding it, could be systemically or locally administered by standard means to any conventional laboratory animal, such as a rat, mouse, rabbit, guinea pig, or dog, before an allogeneic or xenogeneic skin graft, organ transplant, or cell implantation is performed on the animal. Strains of mice such as C57B1-10, B10.BR, and B10.AKM (Jackson Laboratory, Bar Harbor, Me.), which have the same genetic background but are mismatched for the H-2 locus, are well suited for assessing various organ grafts.

Heart Transplantation

A method for performing cardiac grafts by anastomosis of the donor heart to the great vessels in the abdomen of the host was first published by Ono et al. (*J. Thorac. Cardiovasc. Surg.* 57:225, 1969; see also Corry et al., *Transplantation* 16:343, 1973). According to this surgical procedure, the aorta of a donor heart is anastomosed to the abdominal aorta of the host, and the pulmonary artery of the donor heart is anastomosed to the adjacent vena cava using standard microvascular techniques.

Once the heart is grafted in place and warmed to 37° C. with Ringer's lactate solution, normal sinus rhythm will resume. Function of the transplanted heart can be assessed frequently by palpation of ventricular contractions through the abdominal wall. Rejection is defined as the cessation of myocardial contractions, which can be confirmed by under anesthesia. Mutant IL-15 polypeptides would be considered effective in reducing organ rejection if hosts that received injections, for example, of the mutant IL-15 polypeptide experienced longer heart engraftment than the untreated hosts.

Skin Grafting

The effectiveness of mutant IL-15 polypeptides can also be assessed following a skin graft. To perform skin grafts on a rodent, a donor animal is anesthetized and the full thickness skin is removed from a part of the tail. The recipient animal is also anesthetized, and a graft bed is prepared by removing a patch of skin from the shaved flank. Generally, the patch is approximately 0.5×0.5 cm. The skin from the donor is shaped to fit the graft bed, positioned, covered with gauze, and bandaged. The grafts can be inspected daily beginning on the sixth post-operative day, and are considered rejected when more than half of the transplanted epithelium appears to be non-viable. Mutant IL-15 polypeptides would be considered effective in reducing rejection of the skin grafts if hosts that received injections, for example, of the mutant IL-15 polypeptide tolerated the graft longer than the untreated hosts.

Islet Allograft Model

DBA/2J islet cell allografts can be transplanted into rodents, such as 6-8 week-old IL-4$^{-/-}$ and IL-4$^{+/-}$ mice rendered diabetic by a single intraperitoneal injection of streptozotocin (225 mg/kg; Sigma Chemical Co., St. Louis, Mo.). As a control, syngeneic IL-4$^{-/-}$ islet cell grafts can be transplanted into diabetic IL-4$^{-/-}$ mice. Islet cell transplantation can be performed by following published protocols (e.g., see Gotoh et al., *Transplantation* 42:387, 1986). Briefly, donor pancreata are perfused in situ with type IV collagenase (2 mg/ml; Worthington Biochemical Corp., Freehold, N.J.). After a 40 minute digestion period at 37° C., the islets are isolated on a discontinuous Ficoll gradient. Subsequently, 300-400 islets are transplanted under the renal capsule of each recipient. Allograft function can be followed by serial blood glucose measurements (Accu-Check III™; Boehringer, Mannheim, Germany) Primary graft function is defined as a blood glucose level under 11.1 mmol/l on day 3 post-transplantation, and graft rejection is defined as a rise in blood glucose exceeding 16.5 mmol/l (on each of at least 2 successive days) following a period of primary graft function.

Models of Autoimmune Disease

Models of autoimmune disease provide another means to assess polypeptides in vivo. These models are well known to skilled artisans and can be used to determine whether a given mutant IL-15 polypeptide is an immunosuppressant that would be therapeutically useful in treating a specific autoimmune disease when delivered either directly or via genetic therapy.

Autoimmune diseases that have been modeled in animals include rheumatic diseases, such as rheumatoid arthritis (see, e.g., the Example headed "Induction of Collagen-induced Arthritis" below) and systemic lupus erythematosus (SLE), type I diabetes, and autoimmune diseases of the thyroid, gut, and central nervous system. For example, animal models of SLE include MRL mice, BXSB mice, and NZB mice and their F$_1$ hybrids. These animals can be crossed in order to study particular aspects of the rheumatic disease process; progeny of the NZB strain develop severe lupus glomerulonephritis when crossed with NZW mice (Bielschowsky et al., *Proc. Univ. Otago Med. Sch.* 37:9, 1959; see also *Fundamental Immunology*, Paul, Ed., Raven Press, New York, N.Y., 1989). Similarly, a shift to lethal nephritis is seen in the progeny of NBZ×SWR matings (Data et al., *Nature* 263:412, 1976). The histological appearance of renal lesions in SNF$_1$ mice has been well characterized (Eastcott et al., *J. Immunol.* 131:2232, 1983; see also *Fundamental Immunology*, supra). Therefore, the general health of the animal as well as the histological appearance of renal tissue can be used to determine whether the administration of a mutant IL-15 polypeptide can effectively suppress the immune response in an animal model of SLE.

One of the MRL strains of mice that develops SLE, MRL-lpr/lpr, also develops a form of arthritis that resembles rheumatoid arthritis in humans (Theofilopoulos et al., *Adv. Immunol.* 37:269, 1985). Alternatively, an experimental arthritis can be induced in rodents by injecting rat type II collagen (2 mg/ml) mixed 1:1 in Freund's complete adjuvant (100 μl total) into the base of the tail. Arthritis develops 2-3 weeks after immunization. The ability of nucleic acid molecules encoding mutant IL-15 polypeptides to combat the arthritic condition can be assessed by targeting the nucleic acid molecules to T lymphocytes. One way to target T lymphocytes is the following: spleen cell suspensions are prepared 2-3 days after the onset of arthritis and incubated with collagen (100 μg/ml) for 48 hours to induce proliferation of collagen-activated T cells. During this time, the cells are transduced with a vector encoding the polypeptide of interest. As a control, parallel cultures are grown but not transduced, or are transduced with the "empty" vector. The cells are then injected intraperiotoneally is ($5 \times 10^7$ cells/animal). The effectiveness of the treatment is assessed by following the disease symptoms during the subsequent 2 weeks, as described by Chemajovsky et al. (*Gene Therapy* 2:731-735, 1995). Lesser symptoms, compared to control, indicate that the peptide of interest, and the nucleic acid molecule encoding it, function as an immunosuppressant potentially useful in the treatment of autoimmune disease.

The ability of a mutant IL-15 polypeptide to suppress the immune response in the case of Type I diabetes can be tested in the BB rat strain, which was developed from a commercial colony of Wistar rats at the Bio-Breeding Laboratories in Ottawa. These rats spontaneously develop autoantibodies against islet cells and insulin, just as occurs with human Type I diabetes. Alternatively, NOD (non-obese diabetic) mice can be used as a model system.

Autoimmune diseases of the thyroid have been modeled in the chicken. Obese strain (OS) chickens consistently develop spontaneous autoimmune thyroiditis resembling Hashimoto's disease (Cole et al., *Science* 160:1357, 1968). Approximately 15% of these birds produce autoantibodies to parietal cells of the stomach, just as in the human counterpart of autoimmune thyroiditis. The manifestations of the disease in OS chickens, which could be monitored in the course of mutant IL-15 polypeptide treatment, include body size, fat deposit, serum lipids, cold sensitivity, and infertility.

Models of autoimmune disease in the central nervous system (CNS) can be experimentally induced. An inflammation of the CNS, which leads to paralysis, can be induced by a single injection of brain or spinal cord tissue with adjuvant in many different laboratory animals, including rodents and primates. This model, referred to as experimental allergic encephalomyelitis (EAE), is T cell mediated. Similarly, experimentally induced myasthenia gravis can be produced by a single injection of acetylcholine receptor with adjuvants (Lennon et al., *Ann. N.Y. Acad. Sci.* 274:283, 1976).

Autoimmune diseases of the gut can be modeled in IL-2 or IL-10 "knock out" mice, or in mice that receive enemas containing bovine serum albumin.

Nucleic Acid Molecules Encoding Mutant IL-15

The mutant IL-15 polypeptide, either alone or as a part of a chimeric polypeptide, such as those described above, can be obtained by expression of a nucleic acid molecule. Thus, nucleic acid molecules encoding polypeptides containing a mutant IL-15 are considered within the scope of the invention. Just as mutant IL-15 polypeptides can be described in terms of their identity with wild-type IL-15 polypeptides, the nucleic acid molecules encoding them will necessarily have a certain identity with those that encode wild-type IL-15. For example, the nucleic acid molecule encoding a mutant IL-15 polypeptide can be at least 65%, preferably at least 75%, more preferably at least 85%, and most preferably at least 95% (e.g., 99%) identical to the nucleic acid encoding wild-type IL-15. For nucleic acids, the length of the sequences compared will generally be at least 50 nucleotides, preferably at least 60 nucleotides, more preferably at least 75 nucleotides, and most preferably 110 nucleotides.

The nucleic acid molecules of the invention can contain naturally occurring sequences, or sequences that differ from those that occur naturally, but, due to the degeneracy of the genetic code, encode the same polypeptide. These nucleic acid molecules can consist of RNA or DNA (for example, genomic DNA, cDNA, or synthetic DNA, such as that produced by phosphoramidite-based synthesis), or combinations or modifications of the nucleotides within these types of nucleic acids. In addition, the nucleic acid molecules can be double-stranded or single-stranded (i.e., either a sense or an antisense strand).

The nucleic acid molecules of the invention are referred to as "isolated" because they are separated from either the 5' or the 3' coding sequence with which they are immediately contiguous in the naturally occurring genome of an organism. Thus, the nucleic acid molecules are not limited to sequences that encode polypeptides; some or all of the non-coding sequences that lie upstream or downstream from a coding sequence can also be included. Those of ordinary skill in the art of molecular biology are familiar with routine procedures for isolating nucleic acid molecules. They can, for example, be generated by treatment of genomic DNA with restriction endonucleases, or by performance of the polymerase chain reaction (PCR). In the event the nucleic acid molecule is a ribonucleic acid (RNA), molecules can be produced by in vitro transcription.

The isolated nucleic acid molecules of the invention can include fragments not found as such in the natural state. Thus, the invention encompasses recombinant molecules, such as those in which a nucleic acid sequence (for example, a sequence encoding a mutant IL-15) is incorporated into a vector (e.g., a plasmid or viral vector) or into the genome of a heterologous cell (or the genome of a homologous cell, at a position other than the natural chromosomal location).

As described above, the mutant IL-15 polypeptide of the invention may exist as a part of a chimeric polypeptide. In addition to, or in place of, the heterologous polypeptides described above, a nucleic acid molecule of the invention can contain sequences encoding a "marker" or "reporter." Examples of marker or reporter genes include β-lactamase, chloramphenicol acetyltransferase (CAT), adenosine deaminase (ADA), aminoglycoside phosphotransferase (neo$^r$, G418$^r$), dihydrofolate reductase (DHFR), hygromycin-B-phosphotransferase (HPH), thymidine kinase (TK), lacZ (encoding β-galactosidase), and xanthine guanine phosphoribosyltransferase (XGPRT). As with many of the standard procedures associated with the practice of the invention, skilled artisans will be aware of additional useful reagents, for example, of additional sequences that can serve the function of a marker or reporter.

The nucleic acid molecules of the invention can be obtained by introducing a mutation into IL-15-encoding DNA obtained from any biological cell, such as the cell of a mammal. Thus, the nucleic acids of the invention can be those of a mouse, rat, guinea pig, cow, sheep, horse, pig, rabbit, monkey, baboon, dog, or cat. Preferably, the nucleic acid molecules will be those of a human.

Expression of Mutant IL-15 Gene Products

The nucleic acid molecules described above can be contained within a vector that is capable of directing their expression in, for example, a cell that has been transduced with the vector. Accordingly, in addition to mutant IL-15 polypeptides, expression vectors containing a nucleic acid molecule encoding a mutant IL-15 polypeptide and cells transfected with these vectors are among the preferred embodiments.

Vectors suitable for use in the present invention include T7-based vectors for use in bacteria (see, for example, Rosenberg et al., *Gene* 56:125, 1987), the pMSXND expression vector for use in mammalian cells (Lee and Nathans, *J. Biol. Chem.* 263:3521, 1988), and baculovirus-derived vectors (for example the expression vector pBacPAK9 from Clontech, Palo Alto, Calif.) for use in insect cells. The nucleic acid inserts, which encode the polypeptide of interest in such vectors, can be operably linked to a promoter, which is selected based on, for example, the cell type in which expression is sought. For example, a T7 promoter can be used in bacteria, a polyhedrin promoter can be used in insect cells, and a cytomegalovirus or metallothionein promoter can be used in mammalian cells. Also, in the case of higher eukaryotes, tissue-specific and cell type-specific promoters are widely available. These promoters are so named for their ability to direct expression of a nucleic acid molecule in a given tissue or cell type within the body. Skilled artisans are well aware of numerous promoters and other regulatory elements which can be used to direct expression of nucleic acids.

In addition to sequences that facilitate transcription of the inserted nucleic acid molecule, vectors can contain origins of replication, and other genes that encode a selectable marker. For example, the neomycin-resistance (neo$^r$) gene imparts G418 resistance to cells in which it is expressed, and thus permits phenotypic selection of the transfected cells. Those of skill in the art can readily determine whether a given regulatory element or selectable marker is suitable for use in a particular experimental context.

Viral vectors that can be used in the invention include, for example, retroviral, adenoviral, and adeno-associated vectors, herpes virus, simian virus 40 (SV40), and bovine papilloma virus vectors (see, for example, Gluzman (Ed.), *Eukaryotic Viral Vectors*, CSH Laboratory Press, Cold Spring Harbor, N.Y.).

Prokaryotic or eukaryotic cells that contain and express a nucleic acid molecule that encodes a mutant IL-15 polypeptide are also features of the invention. A cell of the invention is a transfected cell, i.e., a cell into which a nucleic acid molecule, for example a nucleic acid molecule encoding a mutant IL-15 polypeptide, has been introduced by means of recombinant DNA techniques. The progeny of such a cell are also considered within the scope of the invention. The precise components of the expression system are not critical. For example, a mutant IL-15 polypeptide can be produced in a prokaryotic host, such as the bacterium *E. coli*, or in a eukaryotic host, such as an insect cell (e.g., an Sf21 cell), or mammalian cells (e.g., COS cells, NIH 3T3 cells, or HeLa cells). These cells are available from many sources, including the American Type Culture Collection (Manassas, Va.). In selecting an expression system, it matters only that the components are compatible with one another. Artisans or ordinary skill are able to make such a determination. Furthermore, if guidance is required in selecting an expression system, skilled artisans may consult Ausubel et al. (*Current Protocols in Molecular Biology*, John Wiley and Sons, New York, N.Y., 1993) and Pouwels et al. (*Cloning Vectors: A Laboratory Manual*, 1985 Suppl. 1987).

The expressed polypeptides can be purified from the expression system using routine biochemical procedures, and can be used as diagnostic tools or as therapeutic agents, as described below.

Mutant IL-15 Polypeptides in Diagnosis

The polypeptide of the invention can be used to diagnose a patient as having a disease amenable to treatment with an IL-15 antagonist. According to this method, a sample of tissue is obtained from the patient and exposed to an antigenically-tagged mutant IL-15 polypeptide. The sample may be any biological sample, such as a blood, urine, serum, or plasma sample. In addition, the sample may be a tissue sample (e.g., biopsy tissue), or an effusion obtained from a joint (e.g., synovial fluid), from the abdominal cavity (e.g., ascites fluid), from the chest (e.g., pleural fluid), from the central nervous system (e.g., cerebral spinal fluid), or from the eye (e.g., aqueous humor). The sample may also consist of cultured cells that were originally obtained from a patient. (e.g., peripheral blood mononuclear cells). It is expected that the sample will be obtained from a mammal, and preferably, that the mammal will be a human patient. If the sample contains cells that are bound by the polypeptide described (i.e., an antigenically-tagged mutant IL-15 polypeptide), it is highly likely that they would be bound by a mutant IL-15 polypeptide in vivo and thereby inhibited from proliferating, or even destroyed, in vivo. The presenting symptoms of candidate patients for such testing and the relevant tissues to be sampled given a particular set of symptoms are known to those skilled in the field of immunology.

Modulation of the Immune Response

Also featured in the invention is a method of suppressing the immune response in a patient by administering a dose of mutant IL-15 that is sufficient to competitively bind the IL-15 receptor complex, and thereby modulate IL-15 dependent immune responses. The polypeptide administered can be a mutant IL-15 polypeptide, including those that are a part of the chimeric polypeptides described above. This method may be used to treat a patient who is suffering from an autoimmune disease, including but not limited to the following: (1) a rheumatic disease such as rheumatoid arthritis, systemic lupus erythematosus, Sjögren's syndrome, scleroderma, mixed connective tissue disease, dermatomyositis, polymyositis, Reiter's syndrome or Behcet's disease (2) type II diabetes (3) an autoimmune disease of the thyroid, such as Hashimoto's thyroiditis or Graves' Disease (4) an autoimmune disease of the central nervous system, such as multiple sclerosis, myasthenia gravis, or encephalomyelitis (5) a variety of phemphigus, such as phemphigus vulgaris, phemphigus vegetans, phemphigus foliaceus, Senear-Usher syndrome, or Brazilian phemphigus, (6) psoriasis, and (7) inflammatory bowel disease (e.g., ulcerative colitis or Crohn's Disease). The administration of the mutant IL-15 polypeptide of the invention may also be useful in the treatment of acquired immune deficiency syndrome (AIDS). Similarly, the method may be used to treat a patient who has received a transplant of biological materials, such as an organ, tissue, or cell transplant. In addition, patients who have received a vascular injury would benefit from this method.

Induction of a Lytic Response

Through the administration of a lytic form of a mutant IL-15 chimeric polypeptide, it is possible to selectively kill autoreactive or "transplant destructive" immune cells without massive destruction of normal T cells. Accordingly, the invention features a method of killing autoreactive or "transplant destructive" immune cells or any malignant cell that expresses the IL-15 receptor in vivo. The method is carried out by administering to a patient an amount of mutant IL-15 linked to a polypeptide that is sufficient to activate the complement system, lyse cells by the ADCC mechanism, or otherwise kill cells expressing the wild-type IL-15 receptor complex. This method can be used, for example, to treat patients who have IL-15R$^+$ leukemia, lymphoma, or other IL-15R$^+$ malignant diseases, such as colon cancer.

Formulations for Use and Routes of Administration

In therapeutic applications, the polypeptide may be administered with a physiologically-acceptable carrier, such as physiological saline. The therapeutic compositions of the invention can also contain a carrier or excipient, many of which are known to skilled artisans. Excipients that can be used include buffers (e.g., citrate buffer, phosphate buffer, acetate buffer, and bicarbonate buffer), amino acids, urea, alcohols, ascorbic acid, phospholipids, proteins (e.g., serum albumin), EDTA, sodium chloride, liposomes, mannitol, sorbitol, and glycerol. The polypeptides of the invention can be formulated in various ways, according to the corresponding route of administration. For example, liquid solutions can be made for ingestion or injection; gels or powders can be made for ingestion, inhalation, or topical application. Methods for making such formulations are well known and can be found in, for example, "Remington's Pharmaceutical Sciences.

Routes of administration are also well known to skilled pharmacologists and physicians and include intraperitoneal, intramuscular, subcutaneous, and intravenous administration. Additional routes include intracranial (e.g., intracisternal or intraventricular), intraorbital, opthalmic, intracapsular, intraspinal, intraperitoneal, transmucosal, topical, subcutaneous, and oral administration. It is expected that the intravenous route will be preferred for the administration of mutant IL-15 polypeptides. The subcutaneous route may also be used frequently as the subcutaneous tissue provides a stable environment for the polypeptide, from which it can be slowly released. Another route of administration of mutant IL-15 polypeptides that has proven feasible is the intraperitoneal route. As described in the examples below, intraperitoneal injection of mutant IL-15/Fc polypeptides is an effective treatment for collagen-induced arthritis (i.e., it delays the onset and decreases the incidence and severity of collagen-induced arthritis). These results demonstrate that systemic administration of mutant IL-15 polypeptides is effective. Thus, while one may target the peptides more specifically to their site of action, such targeting is not necessary for effective treatment. For example, in the event of an autoimmune disease such as rheumatoid arthritis, which affects the joints, mutant IL-15 polypeptides need not be targeted specifically to the joints.

The polypeptides of the invention are less likely to be immunogenic than many therapeutic polypeptides because they can differ from a wild-type polypeptide by only a few amino acid residues. In addition, the mutant IL-15 polypeptides are targeted to cells that express abundant receptors to which they can bind with high affinity.

It is well known in the medical arts that dosages for any one patient depend on many factors, including the general health, sex, weight, body surface area, and age of the patient, as well as the particular compound to be administered, the time and route of administration, and other drugs being administered concurrently. Dosages for the polypeptide of the invention will vary, but can, when administered intravenously, be given in doses of approximately 0.01 mg to 100 mg/ml blood volume. A dosage can be administered one or more times per day, if necessary, and treatment can be continued for prolonged periods of time, up to and including the lifetime of the patient being treated. If a polypeptide of the invention is administered subcutaneously, the dosage can be reduced, and/or the polypeptide can be administered less frequently. Determination of correct dosage for a given application is well within the abilities of one of ordinary skill in the art of pharmacology. In addition, those of ordinary skill in the art can turn to the Examples presented below for guidance in developing an effective treatment regime. For example, one could begin tailoring the dosage of mutant IL-15 polypeptides required for effective treatment of humans from the dosage proven effective in the treatment of small mammals. Mice were effectively treated for an autoimmune condition with daily intraperitoneal injections containing 1.5 μg of mutant IL-15/Fcγ2a. Of course, only routine experimentation would be required to more precisely define the effective limits of any given administrative regime. For example, in a conservative approach, one could define the lowest effective dosage in small mammals, and administer that dose to progressively larger mammals before beginning human safety trials.

EXAMPLES

Reagents

The following reagents were used in the studies described herein: recombinant human IL-2 was obtained from Hoffman-La Roche (Nutley, N.J.); rapamycin was obtained from Wyeth-Ayerst (Princeton, N.J.); cyclosporine-A (CsA) was obtained from Sandoz (East Hanover, N.J.); RPMI-1640 and fetal calf serum (FCS) were obtained from BioWittaker (Walkersville, Md.); penicillin, streptomycin, G418, and strepavidin-RED670 were obtained from Gibco-BRL (Gaithersburg, Md.); dexamethasone, PHA, lysozyme, Nonidet P-40, NaCl, HEPES, and PMSF were obtained from Sigma (St. Louis, Mo.); Ficoll-Hypaque was obtained from Pharmacia Biotech (Uppsala, Sweden); recombinant human IL-15 and anti-human IL-15 Ab were obtained from PeproTech (Rocky Hill, N.J.); anti-FLAG Ab and anti-FLAG-affinity beads were obtained from International Biotechnologies, Inc. (Kodak, New Haven, Conn.); pRcCMV was obtained from InVitrogen Corporation (San Diego, Calif.); genistein was obtained from ICN Biomedicals (Irvine, Calif.); disuccinimidyl suberate (DSS) was obtained from Pierce (Rockford, Ill.); restriction endonucleases were obtained from New England Biolabs (Beverly, Mass.); [$^3$H]TdR was obtained from New England Nuclear (Boston, Mass.); and fluorescent dye conjugated antibodies CD25-PE$^3$, CD14-PE, CD16-PE, CD122-PE, CD4-FITC, CD8-FITC, IgG1-PE or IgG1-FITC were obtained from Beckton/Dickinson (San Jose, Calif.). FLAG peptide was synthesized in the Peptide Synthesis Facility at Harvard Medical School.

Production of FLAG-HMK-IL-15 Fusion Protein

To study the cellular pattern of human IL-15 receptor expression, a plasmid that could be used to express an IL-15 fusion protein was constructed. The plasmid encodes an IL-15 polypeptide having an N-terminus covalently bound to the 18 amino acid FLAG-HMK-sequence (FLAG-HMK-IL-15). FLAG sequences are recognized by biotinylated, highly specific anti-FLAG antibodies (Blanar et al., *Science* 256: 1014, 1992); LeClair et al., *Proc. Natl. Acad. Sci. USA* 89:8145, 1992) while HMK (Heart Muscle Kinase recognition site) sequences allow introduction of radioactive label [$^{32}$P] into the molecule (Blanar et al., supra, LeClair et al., supra).

For the construction of the plasmid FLAG-HMK-IL-15, a 322 bp cDNA fragment encoding mature IL-15 protein was amplified by PCR utilizing synthetic oligonucleotides [sense 5'-GG<u>AATTC</u>AACTGGGTGAATGTAATA-3' (SEQ ID NO:1; EcoRI site (underlined) plus bases 145-162); antisense 5'-CG<u>GGATCC</u>TCAAGAAGTGTTGATGAA-3' (SEQ ID NO:2; BamHI site [underlined] plus bases 472-489)]. The template DNA was obtained from PHA-activated human PBMCs. The PCR product was purified, digested with EcoRI and BamHI, and cloned into the pAR(DRI)59/60 plasmid digested with EcoRI-BamHI as described (Blanar et al., *Science* 256:1014, 1992; LeClair et al., *Proc. Natl. Acad. Sci. USA* 89:8145, 1992). The backbone of the pAR(DRI)59/60 plasmid contains in frame sequences encoding the FLAG and HMK recognition peptide sequences (Blanar et al., *Science* 256:1014, 1992; LeClair et al., *Proc. Natl. Acad. Sci. USA* 89:8145, 1992).

Expression and Purification of FLAG-HMK-IL-15 Fusion Protein

The IL-15-related fusion construct, FLAG-HMK-IL-15, was expressed in BL-21 strain *E. coli* and affinity purified with anti-FLAG coated beads as described (Blanar et al., *Science* 256:1014, 1992; LeClair et al., *Proc. Natl. Acad. Sci. USA* 89:8145, 1992). The fusion protein was eluted from affinity columns after extensive washing with 0.1 M glycine (pH 3.0). The eluate containing FLAG-HMK-IL-15 was dialyzed against a buffer containing 50 mM Tris (pH 7.4) and 0.1 M NaCl for 18 hours at 4° C., filtered through a 0.2 µm membrane, and stored at −20° C.

Analysis of FLAG-HMK-IL-15 Fusion Protein

Figure 1:
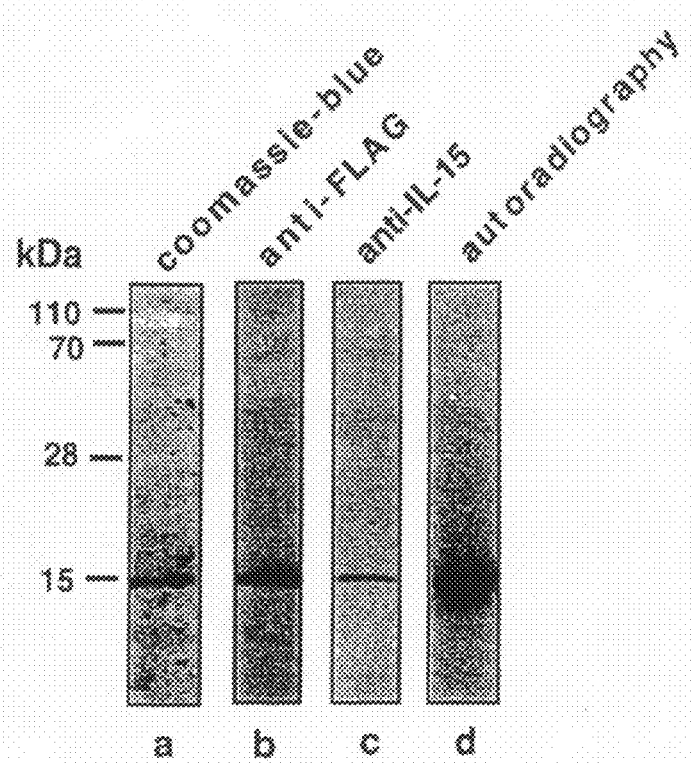
FIG. 1 is a photograph of a Western blot depicting the bacterially-produced, affinity-purified FLAG-HMK-IL-15 fusion protein. Proteins were separated by electrophoresis through a 20% SDS-polyacrylamide gel, visualized by staining with Coomassie blue (lane a) and transferred to PVDF membranes. The membranes were exposed to antibodies against the FLAG peptide (lane b) and human IL-15 (lane c). In lane (d), eluates from an anti-FLAG affinity column were incubated with heart muscle kinase and $[^{32}P]$-γ-ATP for 30 minutes before electrophoresis.

The authenticity of FLAG-HMK-IL-15 fusion protein was confirmed as follows. The proteins present in eluates from the affinity column were separated by SDS-PAGE, transferred to PVDF membranes, and stained with Coomassie blue (FIG. 1, lane a). The presence of FLAG sequences was specifically examined using anti-FLAG Ab (FIG. 1, lane b), and the presence of hIL-15 sequences was specifically examined using anti-hIL-15 Ab (FIG. 1, lane c). A 15 kDa protein, whose mass corresponds to the expected size of FLAG-HMK-IL-15 protein, was identified in each of these analyses. To confirm that the fusion protein contains the HMK recognition site, eluates from the affinity column were incubated in the presence of enzymatically active HMK and radioactive [$^{32}$P]-γ-ATP, followed by separation of proteins by SDS-PAGE. Autoradiography again identified a single radiolabeled 15 kDa band that co-migrates with the FLAG-HMK-IL-15 (FIG. 1, lane d). Thus, the kDa protein contains all three elements of the designed fusion protein: FLAG sequence, HMK sequence, and hIL-15 sequence.

Cell Culture

Human PBMCs

Human peripheral blood mononuclear cells (PBMCs) were obtained from leukophoresis preparations from healthy donors and isolated by Ficoll-Hypaque density gradient centrifugation according to standard protocols.

PBMCs were maintained at 37° C. in an atmosphere containing 5% CO$_2$ in RPMI-1640 medium supplemented with 10% FCS, penicillin (0.5 U/ml), and streptomycin (0.5 µg/ml).

For studies involving rapamycin or genistein, human PBMCs (4×10$^5$/well) were plated in U-bottomed 96-well tissue culture plates (NUNC; Naperville, Ill.) with rapamycin (10 ng/ml), genistein (10 µg/ml) or media alone, and cultured for 3 days at 37° C. and 5% CO$_2$. Cell viability was tested utilizing the standard trypan blue exclusion method (*Current Protocols in Immunology*, Vol. 3, ed. R. Coico, New York: John Wiley & Sons, 1995).

BAF-BO3 Cells

The BAF-BO3 cell line is an IL-3-dependent, murine pro-B cell line. A BAF-BO3 cell line that was pre-selected for high expression of the IL-2Rα subunit was kindly provided by T. Taniguchi (Osaka, Japan; Hatakeyama et al., *Cell* 59:837, 1989). BAF-BO3 cells were transfected with vector control (pRcCMV-0) or cDNA encoding the human IL-2Rβ subunit cloned into pRcCMV (pRcCMV-IL-2Rβ), by electroporation at 350 volts and 500 µFarads using 20 µg of ScaI linearized plasmid. Transfected cells were selected in the presence of 1 mg/ml G418 and tested for the expression of the IL-2Rβ subunit by fluorescence activated cell sorting (FACS) analysis as described (Maslinski et al., *Int. Immunol.* 4:509, 1992; Hataleyama et al., *Cell* 59:837, 1989).

BAF-BO3 cells were maintained at 37° C. with 5% CO$_2$ in RPMI-1640 medium supplemented with 10% FCS, penicillin (0.5 U/ml), streptomycin (0.5 µg/ml), and 5% (V/V) IL-3 rich WEHI cell supernatant (Hatakeyama et al., *Cell* 59:837, 1989).

To test mutant polypeptides, a cytotoxic T lymphocyte cell line, CTLL-2, can also be used. This cell line is available from the American Type Culture Collection (12301 Parklawn Drive, Rockville, Md. 20852-1776).

Cellular Proliferation Assays

Human PBMCs

Peripheral blood mononuclear cells ($1\times10^6$/ml) were stimulated with PHA (2 μg/ml) for 72 hours at 37° C. in RPMI-1640 medium supplemented with 10% FCS, penicillin, and streptomycin, as described above. To investigate the effect of immunosuppressive drugs, aliquots of cells ($10^6$ PBMCs/ml) were preincubated with cyclosporin-A (CsA; 150 ng/ml), rapamycin (5 ng/ml), or dexamethasone (0.1 mg/ml) for 20 minutes before the addition of PHA.

In some experiments, cells prepared as described above were washed after 72 hours in culture, plated in U-bottomed 96-well tissue culture plates at $2\times10^5$ PBMCs per well (NUNC, Naperville, Ill.), and then re-stimulated with one of the following reagents: PHA (2 μg/ml), FLAG peptide ($10^{-4}$ M), IL-2 (100 U/ml), or FLAG-HMK-IL-15 (100 μl/ml) for 72 hours. Cells were "pulsed" for 4 hours with 1 μCi of [$^3$H]TdR (New England Nuclear, Boston, Mass.), harvested onto Whatman 934-AH glass microfiber filters, and hypotonically lysed using a PHD Cell Harvester (Cambridge Technology, Inc., Cambridge, Mass.). Cell associated [$^3$H]-TdR was measured using a Beckman LS 2800 scintillation counter (Beckman, Fullerton, Calif.).

BAF-BO3 Cells

IL-3 dependent BAF-BO3 cells, which constitutively express the IL-2Rγ subunit, were transfected with a control pRcCMV construct (pRcCMV-0) or a pRcCMV construct containing cDNA encoding the full-length human IL-2Rβ_ subunit and the neo$^r$ gene (pRcCMV-IL-2Rβ). G418 resistant clones were then selected. Cells that were selected in this way were used to test the biological activity of FLAG-HMK-IL-15. This strategy has been used to identify cells transfected with cDNA encoding full-length IL-2Rβ subunits, and which, therefore, proliferate in response to exogenously added human IL-2 or IL-15 (Giri et al., *EMBO J.* 13:2822, 1994). Cells were washed twice to remove the medium containing the growth factor IL-3, and starved for 16 hours in RPMI-1640 medium supplemented with 10% FCS, penicillin (0.5 U/ml), and streptomycin (0.5 μg/ml). Cells were then plated at $2\times10^4$ cells/well, stimulated with FLAG-HMK-IL-15, and cultured for 72 hours at 37° C. in an atmosphere containing 5% $CO_2$. This was followed by a 14 hour "pulse" with 1 μCi of [$^3$H]-TdR. The BAF-BO3 cells were then harvested and cell-associated radioactivity was measured by scintillation counting as described above.

Cross-Linking Activated PBMCs Cultured with FLAG-HMK-IL-15

After 72 hours in culture, PHA-activated PBMCs were washed twice in cold phosphate-buffered saline (PBS), and $10^7$ cells/ml were incubated for 30 minutes at 4° C. in 400 μl of RMPI-1640 medium supplemented with 25 mM HEPES (pH 7.4), 10% FCS, penicillin (0.5 U/ml), and streptomycin (0.5 μg/ml). Supplemented RPMI-1640 medium (20 μl) containing 1 μg of recombinant human IL-15 as a control for non-specific binding or medium alone was then added, and the incubation was continued for 15 minutes before 20 μl of medium containing [$^{32}$P]-labeled FLAG-HMK-IL-15 (1 ng, 500,000 cpm) was added to each sample. After further incubation for 1 hour at 4° C., the cells were washed with PBS and resuspended in 250 μl of PBS. Disuccinimidyl suberate (DDS; 1 mM), a cross-linker, was added, and cross-linking was performed as described by Tsudo et al. (*Proc. Natl. Acad. Sci. USA* 83:9694, 1986). The cross-linked cells were collected by centrifugation, washed, solubilized with extraction buffer (2% Nonidet P-40, 0.14 M NaCl, 25 mM HEPES (pH 7.4), 1 mM phenyl-methylsulfonyl fluoride) and centrifuged. Proteins present in the supernatants of these cell lysates were separated by 8% SDS-PAGE under reducing conditions. An autoradiogram was developed from the dry gel after exposure at −70° C. overnight.

Cell Staining for Flow Cytometry

Resting or PHA-activated PBMCs ($3\times10^5$ cells/tube) were washed twice with ice-cold PBS/0.02% sodium azide and incubated in medium containing FLAG-HMK-IL-15 (0.1 μg/100 μl) or, as a control, in medium alone. The incubation was carried out on ice for 30 minutes. The cells were then washed with PBS and incubated for two sequential 30 minute periods at 4° C. with biotin-conjugated anti-FLAG monoclonal antibody (0.5 μg/100 μl) and streptavidin-RED670 (0.5 μg/100 μl). The cells were then counterstained with CD25-PE, CD14-PE, CD16-PE, CD122-PE, CD4-FITC, or CD8-FITC, as indicated. Addition of IgG1-PE or IgG1-FITC was added to cell populations that had not been incubated with any of the aforementioned reagents in order to identify non-specific binding. Cell surface phenotype was analyzed using FACScan (Becton/Dickinson, Calif.) and Cell Quest software.

FLAG-HMK-IL-15 Binds the IL-15Rα Subunit

Figure 2:
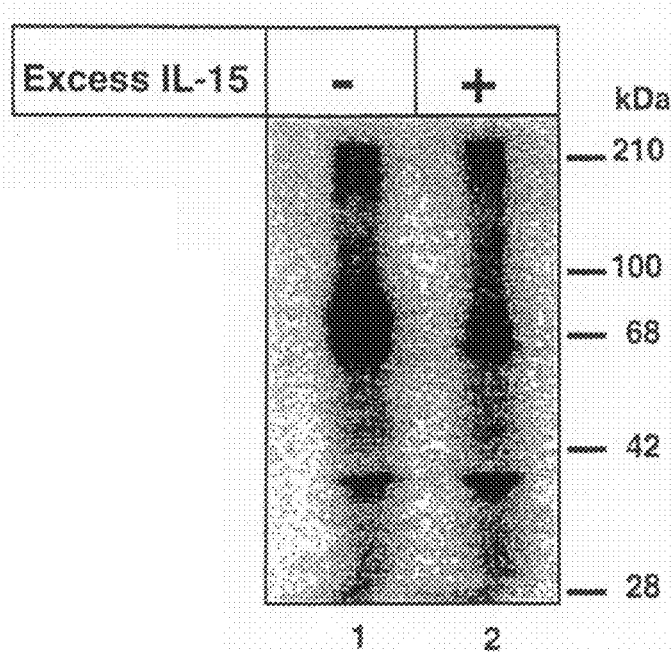
FIG. 2 is an autoradiograph depicting proteins that were extracted from PHA-stimulated PBMCs that were incubated with $[^{32}P]$-FLAG-HMK-IL-15, cross-linked with DSS, and separated by SDS-PAGE under reducing conditions. A 75-80 Kda band is apparent (lane 1). To control for nonspecific cross-linking, replicates were incubated with $[^{32}P]$-FLAG-HMK-IL-15 in the presence of a molar excess of IL-15 (lane 2).

The purified FLAG-HMK-IL-15 fusion protein was tested to determine whether it interacts with cell surface IL-15 receptors. As described above, [$^{32}$P]-FLAG-HMK-IL-15 was added to cultures of PBMCs that were activated by a mitogen, PHA. In order to permanently bind interactive proteins to one another, the chemical cross-linker disuccinimidyl suberate (DSS) was added. The cells were washed, lysed, centrifuged, and detergent-soluble proteins were separated by SDS-PAGE. Autoradiography of SDS-PAGE separated proteins revealed a single 75-80 kDa band corresponding to the combined molecular weight of FLAG-HMK-IL-15 (15 kDa) and the human IL-15Rα subunit (60-65 kDa; FIG. 2, lane 1). The identity of this band as the IL-15Rα subunit was confirmed by cross-linking experiments conducted in the presence of a molar excess of hIL-15. Under these conditions, we failed to detect the radiolabeled 15 kDa band (FIG. 2, lane 2). Thus, the conformation of [$^{32}$P]-FLAG-HMK-IL-15 fusion proteins allows site specific binding to the 60-65 kDa IL-15Rα subunit expressed on the surface of mitogen-activated PBMCs.

FLAG-HMK-IL-15 is a Biologically Active Growth Factor that Requires Expression of IL-2Rβ

Figure 3A:
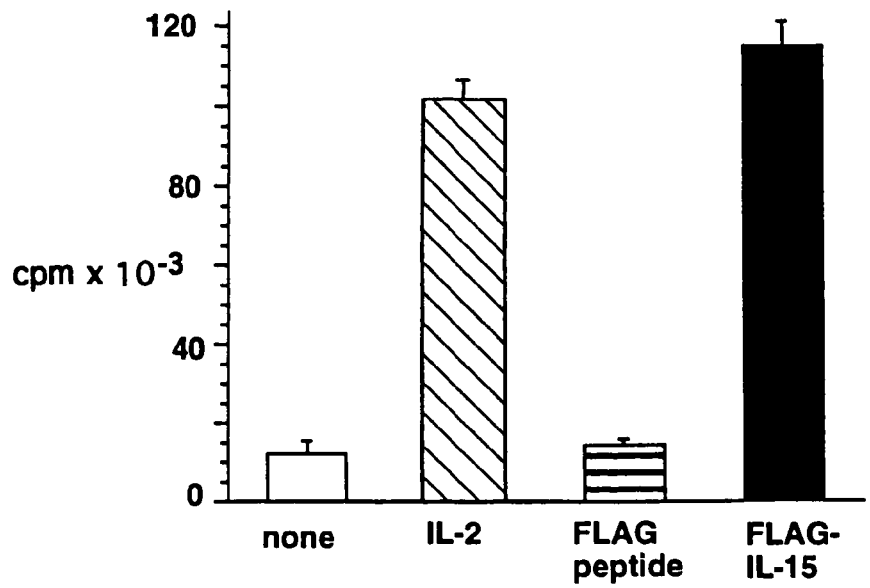
FIG. 3A is a bar graph depicting the mitogenic response of PHA-stimulated PBMCs that were stimulated with either buffer alone ("none"), FLAG peptide ($10^{-4}$ M), IL-2 ($10^{-9}$ M) or FLAG-HMK-IL-15 ($10^{-9}$ M). The cultured cells were "pulsed" with $[^{3}H]$-TdR, and the amount of incorporated radioactivity was determined by scintillation counting.
Figure 3B:
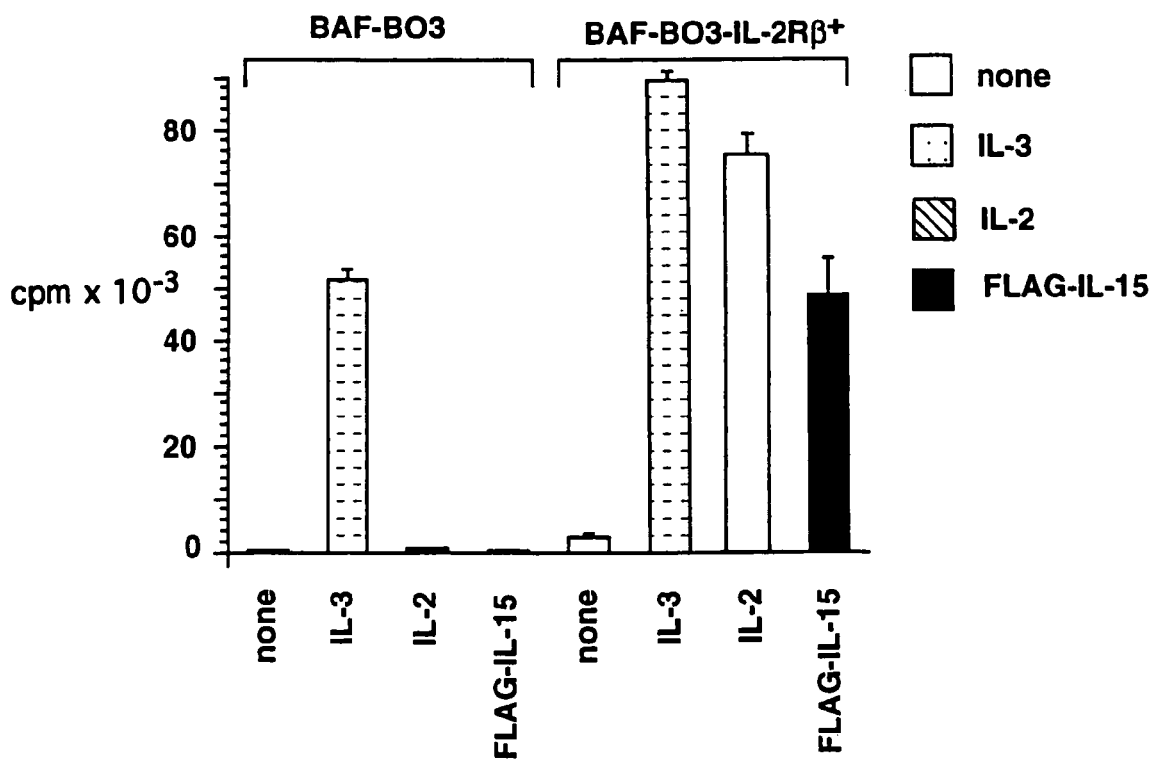
FIG. 3B is a bar graph depicting the mitogenic response of BAF-BO3 cells transfected with pRcCMV (control; left-hand panel) or with Prccmv-IL-2Rβ (encoding the wild-type human IL-2Rβ subunit; right-hand panel) and incubated with medium alone ("none"), media containing IL-3, IL-2 (50 U/ml), or FLAG-HMK-IL-15 (10 ng/ml), and pulsed with $[^{3}H]$-TdR (b). The cultured cells were "pulsed" with $[^{3}H]$-TdR, and the amount of incorporated radioactivity was determined by scintillation counting.

In the next series of experiments, the FLAG-HMK-IL-15 fusion protein was tested in order to determine whether it could function as a biologically active growth factor. PHA-activated human PBMCs proliferate in response to either FLAG-HMK-IL-15 or human recombinant IL-2, as detected via the [$^3$H]-TdR incorporation assay described above. A FLAG peptide lacking the IL-15 sequence does not stimulate cell proliferation (FIG. 3a). As does IL-2, the FLAG-HMK-IL-15 fusion protein stimulates proliferation of IL-2Rγ$^+$BAF-BO3 cell transfectants that express the IL-2Rβ subunit (FIG. 3b, right-hand panel). The FLAG-HMK-IL-15 fusion protein does not, however, stimulate the proliferation of parental BAF-BO3 cells that were transfected with a vector lacking IL-2Rβ chain sequences (FIG. 3b, left-hand panel). Thus, FLAG-HMK-IL-15 is a biologically active growth factor that requires expression of IL-2Rβ chains upon target cells in order to stimulate cellular proliferation.

Mitogen-Activated, but not Resting, PBMCs Express the IL-15Rα Subunit

Figure 4A:
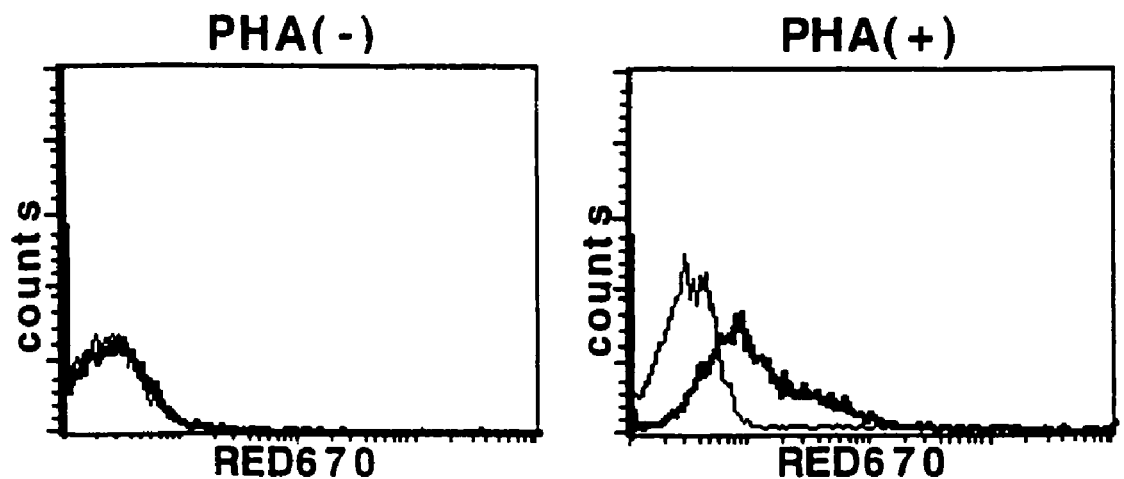
FIGS. 4A-4C are a series of plots depicting the expression of IL-15Rα_subunits on human PBMCs by flow cytometry analysis of stained cells. Freshly isolated or PHA pre-activated PBMCs were washed and incubated with medium alone (thin line) or FLAG-HMK-IL-15 (thick line) followed by anti-FLAG biotinylated Ab and Streptavidin-RED670 (FIG. 4A). The data presented in FIG. 4B were obtained from washed PBMCs that were preincubated with media alone (left-hand side) or media containing 2 μg of human recombinant IL-15 (right-hand side) for 20 minutes at 4° C. before the addition of FLAG-HMK-IL-15. For simplicity, graphs represent specific binding of FLAG-HMK-IL-15; non-specific binding was subtracted. The data presented in FIG. 4C were obtained from PBMCs that were preincubated with phycoerythrin conjugated anti-CD4 or anti-CD8 for 30 minutes before the addition of FLAG-HMK-IL-15.
Figure 4B:
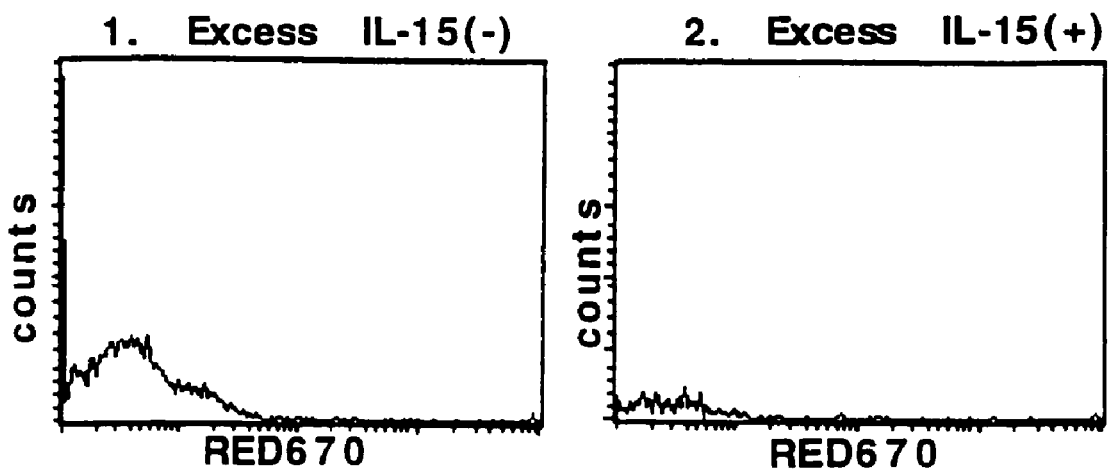
Figure 4C:
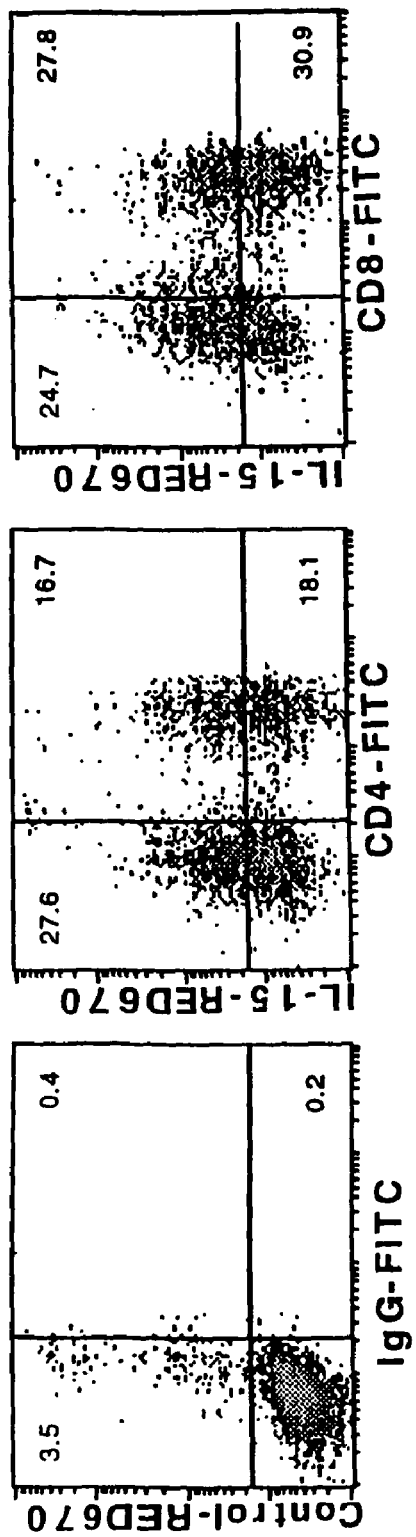

The FLAG-HMK-IL-15 fusion protein, biotinylated anti-FLAG antibody, and streptavidin-RED670 were employed to detect expression of IL-15 binding sites on human PBMCs by cytofluorometric analysis. The PBMCs tested were either freshly isolated or PHA-activated. These cells were washed and incubated with either medium alone or FLAG-HMK-IL-15 followed by anti-FLAG biotinylated Ab and streptavidin-RED670. The stained cells were analyzed by flow cytometry (FIG. 4A). PBMCs that were activated with PHA expressed IL-15Rα proteins but resting PBMCs did not. In keeping with the result of the cross-linking experiments described above (FIG. 2), binding of FLAG-HMK-IL-15 to PHA activated PBMCs is blocked by a molar excess of rIL-15 (FIG. 4B), thereby demonstrating the specificity of FLAG-HMK-IL-15 binding for IL-15 binding sites. Both activated CD4$^+$ and CD8$^+$ cells express IL-15α chains (FIG. 4C); Activation induced IL-15α chains were also detected on CD14$^+$ (monocyte/macrophage) cells and CD16$^+$ (natural killer) cells.

IL-2Rα and IL-2Rβ Subunits are not Required for IL-15 Binding

Figure 5A:
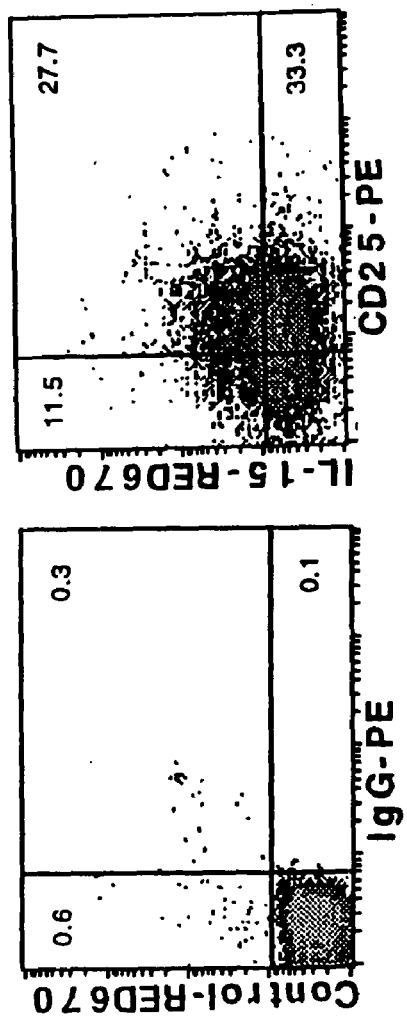
FIGS. 5A-5C are a series of plots generated by fluorescence activated cell sorting (FACS) analysis of PHA-activated PBMCs stained with FLAG-HMK-IL-15 proteins and anti-CD25 IL-2Rα chain) monoclonal antibodies.
Figure 5B:
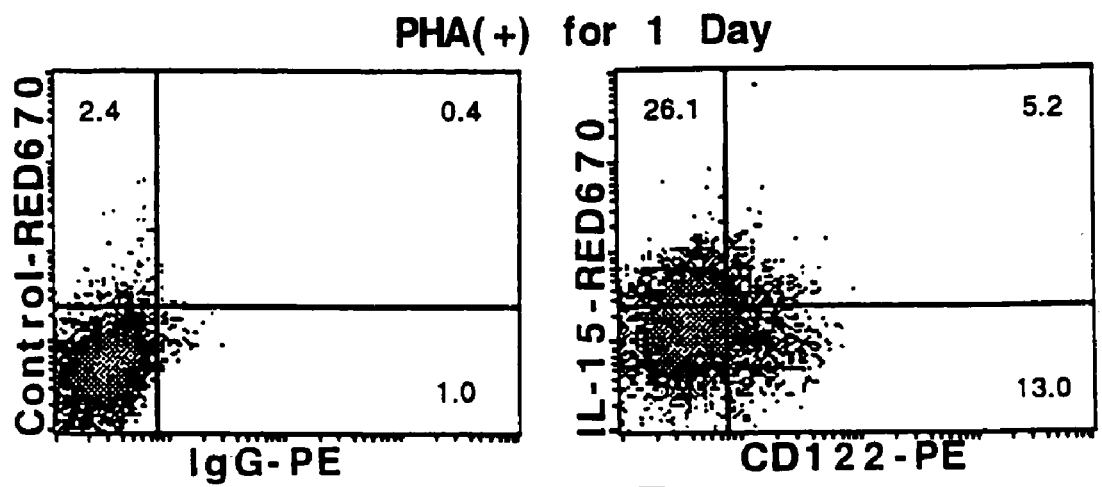

FACS analysis of PHA-activated PBMCs stained with FLAG-HMK-IL-15 proteins and anti-CD25 Mab, against the IL-2Rα subunit, reveals cell populations expressing both IL-15Rα and IL-2Rα subunits, as well as cell populations that express either subunit, but not both (FIG. 5A). There are IL-2Rα$^+$ cells that do not bind FLAG-HMK-IL-15 (FIG. 5A). Almost all PBMCs that were stimulated with PHA for only one day express either IL-15Rα or IL-2Rβ chains, but not both proteins (FIG. 5B). In contrast, 3 days following PHA stimulation, a far larger population of IL-15Rα$^+$, IL-2Rβ$^+$ cells (double positive) and a far smaller population of IL-15Rα$^+$, IL-2Rβ$^+$ cells (single positive) were noted (FIG. 5B). Interestingly, there are IL-2Rβ$^+$ cells that fail to bind IL-15 (FIG. 5B). Therefore, expression of IL-2Rβ chains is not sufficient for IL-15 binding.

Taken together, these data indicate that IL-15 can bind IL-15Rα$^+$, IL-2Rα$^-$, IL-2Rβ$^-$ cells. A similar conclusion was reached through experimentation that probed the interaction of IL-15 with IL-2Rα$^-$, β$^-$ cells transfected with IL-15Rα subunit (Anderson et al., *J. Biol. Chem.* 270:29862, 1995; Giri et al., *EMBO J.* 14:3654, 1995).

Figure 5C:
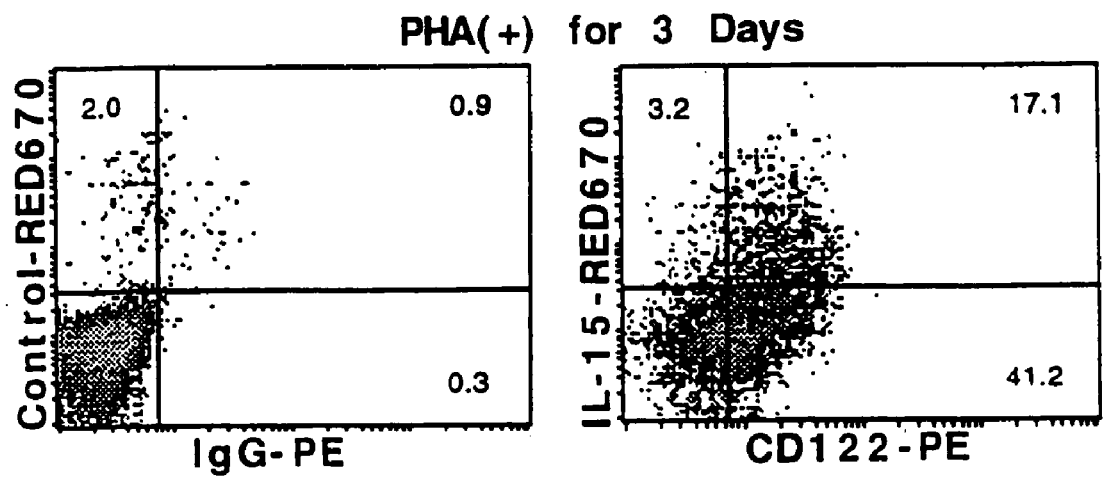

In addition to the requirement for IL-15Rα subunit expression, the IL-2Rβ and IL-2Rγ subunits are required to render cells sensitive to IL-15 triggered growth (FIG. 3, see also FIG. 5).

Figure 6A:
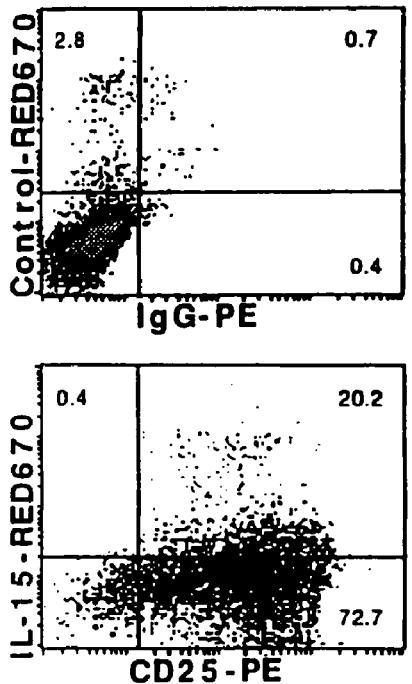
FIGS. 6A-6D are a series of plots generated by fluorescence activated cell sorting (FACS). To determine the effect of immunosuppressant drugs on the mitogen-induced expression of IL-15Rα, PBMCs were preincubated with cyclosporin (CsA.
Figure 6B:
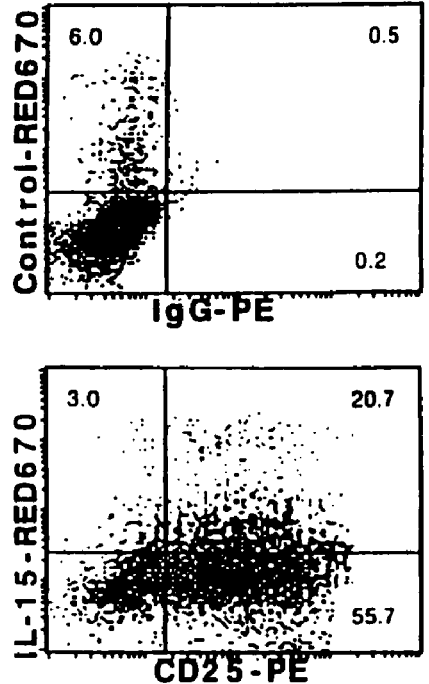
Figure 6C:
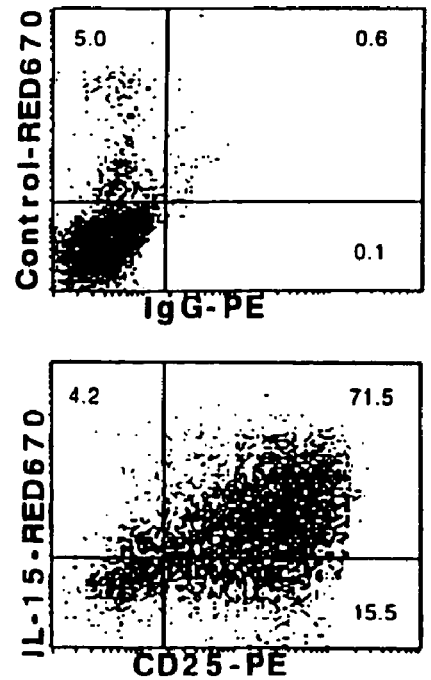
Figure 6D:
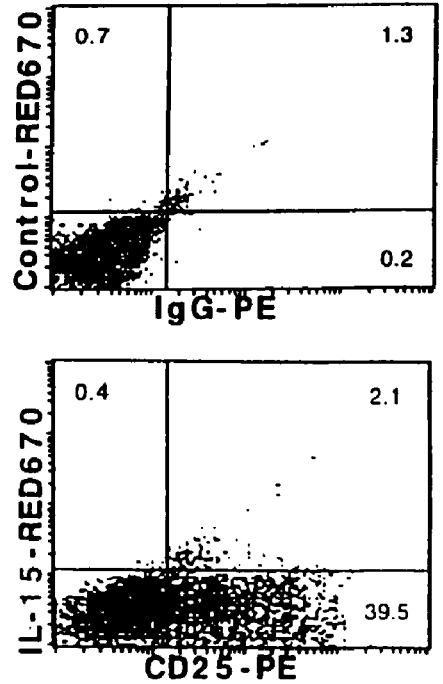
Figure 7:
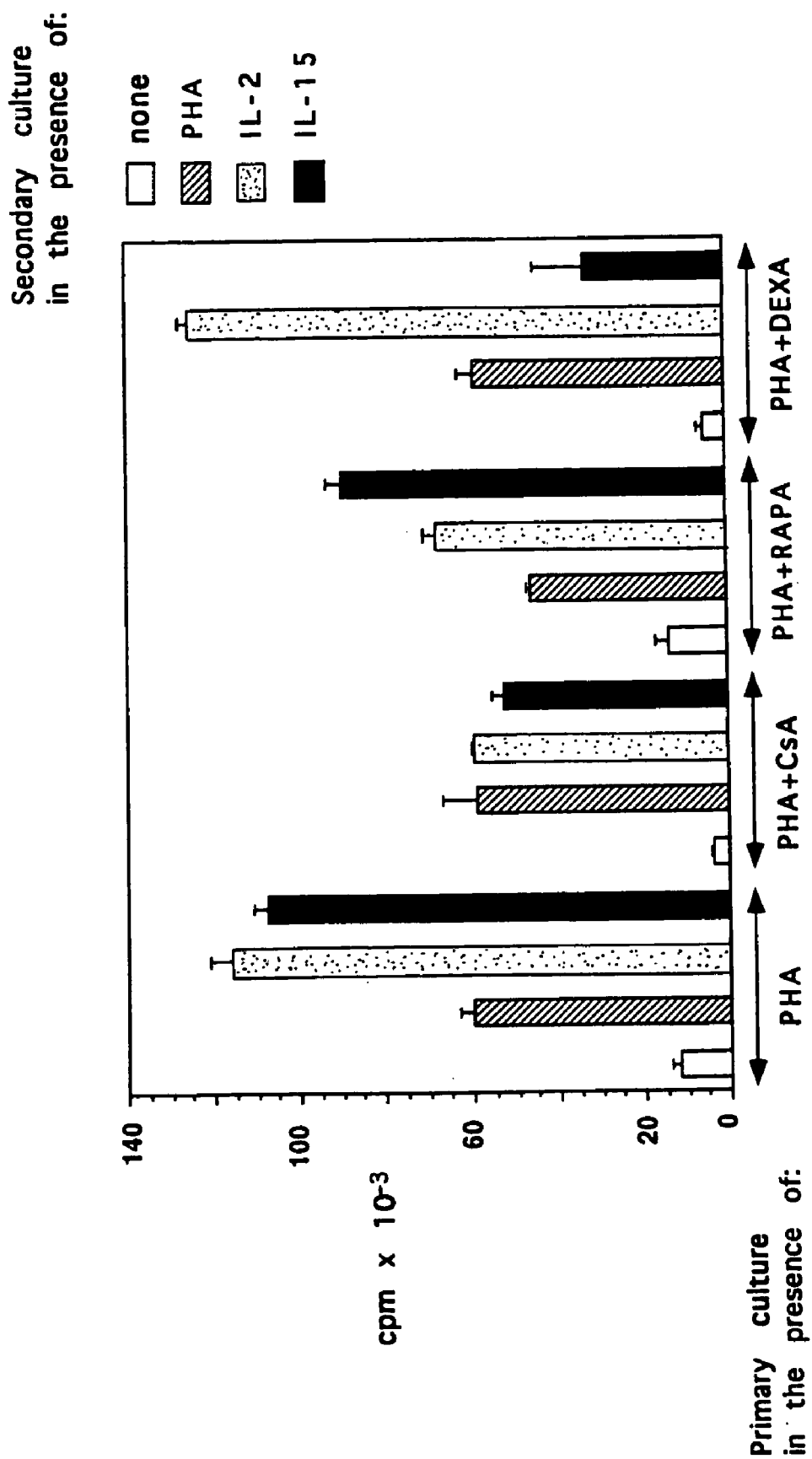
FIG. 7 is a bar graph depicting the proliferative response of human PBMCs that were pre-treated with immunosuppressive drugs and PHA and then treated with PHA, IL-2 or IL-15. Cells were harvested after a 4 hour pulse of [$^3$H]-TdR and cell-incorporated radioactivity was measured in a scintillation counter.

Dexamethasone, but not Cyclosporine or Rapamycin Blocks Mitogen-Induced Expression of the IL-15Rα Subunit The effects of several immunosuppressive drugs on PHA-induced expression of IL-15Rα by PBMCs were also studied. The drugs tested were cyclosporine-A (CsA), rapamycin, and dexamethasone. The addition of CsA to PBMCs cultured with PHA resulted in a 20% reduction in the expression of IL-2Rα, but IL-15Rα was unaffected (FIG. 6). The addition of rapamycin actually resulted in enhanced IL-15Rα expression (FIG. 6C). In contrast to the effects of CsA and rapamycin, dexamethasone powerfully blocked the expression of IL-15Rα chains on mitogen activated PBMCs (FIG. 6D). In accordance with these data, PHA-activated, dexamethasone-treated cells proliferated poorly in response to IL-15, while the response to IL-2 was not inhibited by dexamethasone (FIG. 7). In this experiment, PMBCs were cultured in the presence of PHA and various immuno-suppressive drugs, and then washed and cultured further in the presence of medium alone ("none"), PHA, IL-2, or IL-15 for 2 days before a [$^3$H]-TdR pulse. The potent response of PHA-activated, dexamethasone-treated PBMCs to IL-2 proves that the ability of dexamethasone to inhibit the proliferative response to IL-15 is not due to a non-specific toxic effect.

The studies described above used FLAG-HMK-IL-15 and flow cytometry analysis to determine whether resting and mitogen-activated PBMCs express the IL-15Rα subunit. The IL-15Rα subunit is rapidly expressed by activated but not resting lymphocytes, NK-cells, and macrophages (FIG. 4).

These studies have also shown that the induction of IL-15Rα by mitogen is sensitive to an immunosuppressant: PBMCs pre-treated with dexamethasone and stimulated with PHA do not express IL-15Rα as vigorously as cells that were not pre-treated with dexamethasone (FIG. 6). Similarly, PBMCs pre-treated with dexamethasone do not proliferate as robustly in response to exogenously added IL-15 (FIG. 7). The cells do respond partially to IL-15. This may reflect that fact that IL-15Rα is expressed within 24$^+$ hours of dexamethasone withdrawal. CsA, a potent inhibitor of IL-2 and IL-15Rα expression (Farrar et al., *J. Biol. Chem.* 264:12562, 1989), is ineffective in preventing the mitogen-induced expression of the IL-15Rα chain (FIG. 6). There was a slight reduction in the proliferative response to exogenously added IL-15 among cells pre-treated with CsA for 72 hours (FIG. 7), however this reduction may be due to inhibition of any number of events in the CsA-sensitive, Ca$^{2+}$-dependent pathway of T cell activation. Since the same modest reduction in cell proliferation was observed in response to IL-2, CsA may exert certain long lasting effects by blocking signaling pathway(s) shared by IL-2 and IL-15. These results, in conjunction with the data showing CsA-independent induction of IL-15 gene expression, suggest that CsA may not block IL-15 triggered immune responses. On the contrary, efficiently blocking the induction of the IL-15Rα subunit with dexamethasone may be very helpful in preventing IL-15 induced cellular proliferation.

In summary, the experiments presented above have demonstrated that: (i) IL-15Rα subunits are rapidly expressed by activated macrophages, T cells, and NK cells, and (ii) induction of the IL-15Rα subunit is blocked by dexamethasone but not by CsA or rapamycin. In addition, the experiments have confirmed that the IL-15Rα subunit is necessary and sufficient for IL-15 binding and that the FLAG-HMK-IL-15 fusion protein is an extremely useful tool for studying IL-15 receptors.

A Comparative Analysis of the IL-2 and IL-15 Signalling Pathways

In this series of experiments, the intracellular signalling pathway that is initiated when IL-2 binds to the IL-2Rα, -β, -γ receptor complex was compared to the pathway initiated when IL-15 binds to the receptor complex composed of IL-15Rα, IL-2Rβ, and IL-2Rγ.

The methods, in addition to those described above, required to perform these experiments follow.

Cell Culture, Cell Lysis and Protein Immunoblotting

Fresh human PBMCs were isolated as described above and cultured in RPMI-1640 medium supplemented with 10% FCS, penicillin, and streptomycin (also as above). To achieve activation by a mitogen, PHA (10 µg/ml) was added to the culture for 3 days. PHA-stimulated PBMCs were washed three times with PBS, cultured for 14 hours in RPMI-1640 medium containing 10% FCS, penicillin, and streptomycin, then cultured in medium containing recombinant human IL-2 (100 U/ml), recombinant human IL-15 (10 ng/ml) or non-supplemented medium, for 10 minutes at 37° C.

After stimulation with interleukins, the cells were washed in cold PBS and lysed in an ice-cold lysis buffer (150 mM NaCl, 20 mM Tris (pH 7.5), 1 mM phenylmethylsulfonyl fluoride, 0.5 mg/ml leupeptin, 10 mg/ml aprotinin, 1 mM Na$_3$VO$_4$, 50 mM NaF, and 1% NP-40). Lysates were incubated for 15 minutes on ice and then pelleted at 100,000×g for 30 minutes.

Soluble proteins were separated by SDS-PAGE (10% acrylamide) followed by transfer to a PVDF membrane (Millipore, Bedford, Mass.). The membrane was then incubated in blocking buffer (25 mM HEPES (pH 7.4), 150 mM NaCl, 0.05% Tween, and 2% BSA) for 2 hours at room temperature, followed by incubation with an anti-phosphotyrosine antibody, RC-20, conjugated to alkaline phosphate (Signal Transduction Labs, Inc. Lexington, Ky.) for 2 hours at room temperature. Washed blots were developed in the BCIP/NBT phosphatase substrate solution for calorimetric analysis (Kirkegard and Perry Laboratories, Inc. Gaithersburg, Md.).

The Pattern of Tyrosine Phosphorylated Proteins Induced by IL-2 is the Same as that Induced by IL-15

Figure 8A:
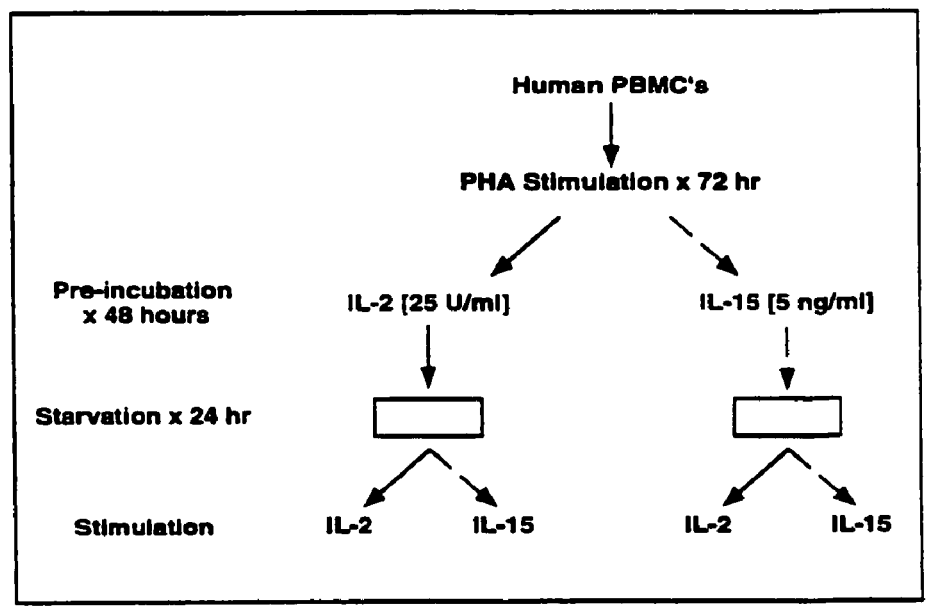
FIG. 8A is a diagram of the protocol used to induce IL-2 and IL-15 responsive PBMCs.
Figure 8B:
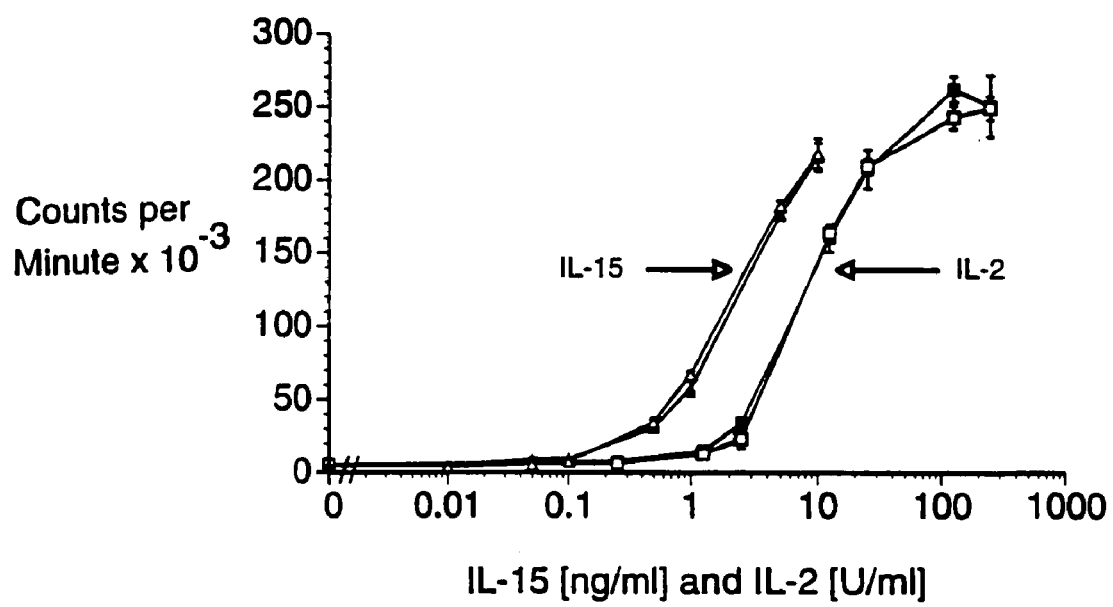
FIG. 8B is a graph depicting the proliferative response of PBMCs that were pre-stimulated with PHA for 3 days and then cultured in the presence of IL-2 (Δ; □) or IL-15 (▲; ■) for 2 days, and then tested for secondary response to IL-2 or IL-15 according to the protocol illustrated in FIG. 8A. Arrow indicates that the cytokine was present during secondary stimulation. Error bars indicate the mean±standard deviation.

To select a population of activated, IL-2 responsive T cells, PBMCs were stimulated with PHA for 3 days, washed, and then stimulated with IL-2 or IL-15 for an additional 2 days. Cultivation of lymphocytes in IL-2 rich medium leads to propagation of lymphocytes that express a high copy number of the tri-molecular high-affinity IL-2R complex (Maslinski et al., *J. Biol. Chem.* 267:15281, 1992). Furthermore, cultivation of PHA-treated PBMCs with IL-2 or IL-15 propagates cells that are equally sensitive to further stimulation with either cytokine. Hence, according to the scheme shown in FIG. 8A, stimulation of mitogen-activated PBMCs with IL-2 or IL-15 does not select for a bulk cell population that then responds only to IL-2 or only to IL-15.

Figure 9:
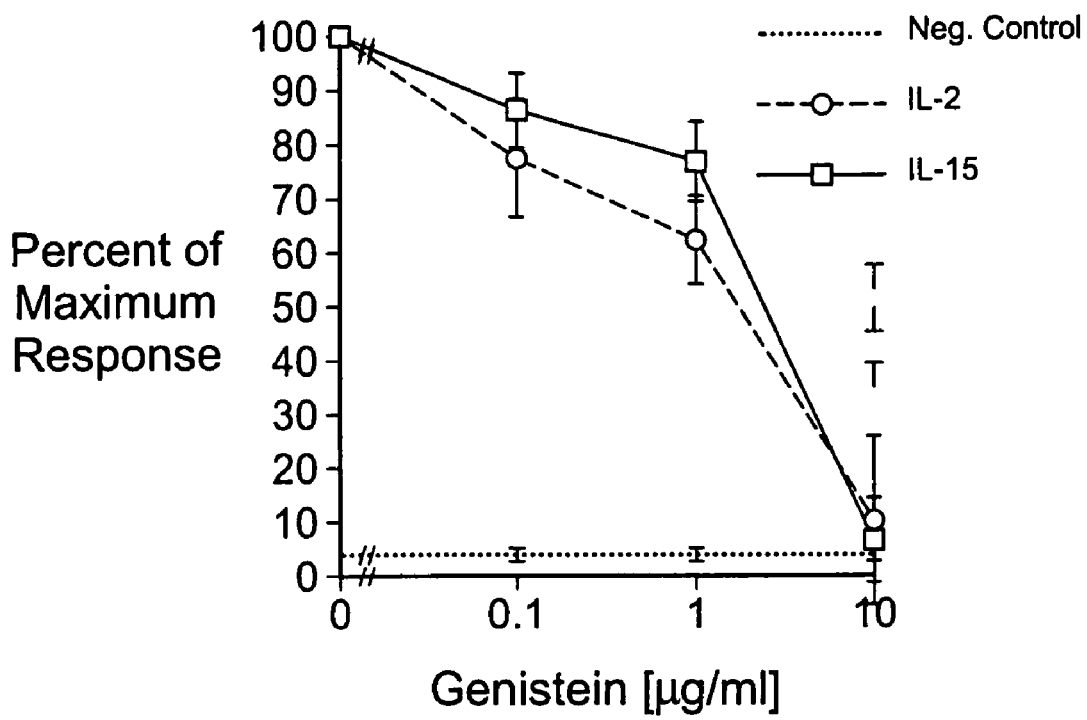
FIG. 9 is a line graph. PHA-stimulated PBMCs were incubated with genistein at various doses for 15 minutes at 37° C. followed by stimulation with IL-2 or IL-15 for 38 hours in a standard proliferation assay. Control cells were not treated with genistein. Error bars indicate the mean±standard deviation.

Further experiments were carried out using T cells prestimulated with PHA for 3 days followed by stimulation with IL-2 for 2 days. IL-2 stimulated cell proliferation is a protein tyrosine kinase dependent event (Maslinski et al. *J. Biol. Chem.* 267:15281, 1992); Remillard et al., *J. Biol. Chem.* 266:14167, 1991). Thus, an inhibitor of tyrosine kinases, genistein, was used to test whether the proliferative signals induced by IL-15 are mediated by the same tyrosine kinases as are the proliferative signals induced by IL-2. IL-2 and IL-15 both induce T cell proliferation and both manifest a similar dose-related sensitivity to genistein (FIG. 9).

To rule out the possibility that genistein was functioning as a general toxin, rather than a selective inhibitor of protein kinase-dependent IL-2 or IL-15-induced cell proliferation, a standard trypan blue exclusion assay was performed. Cell viability after 3 days of incubation in the presence of genistein (10 µg/ml) was 659±15% of the control (where no genistein was added). Therefore, most of the observed inhibitory effect of genistein is due to inhibition of IL-2 and IL-15 triggered signal transduction.

Figure 10:
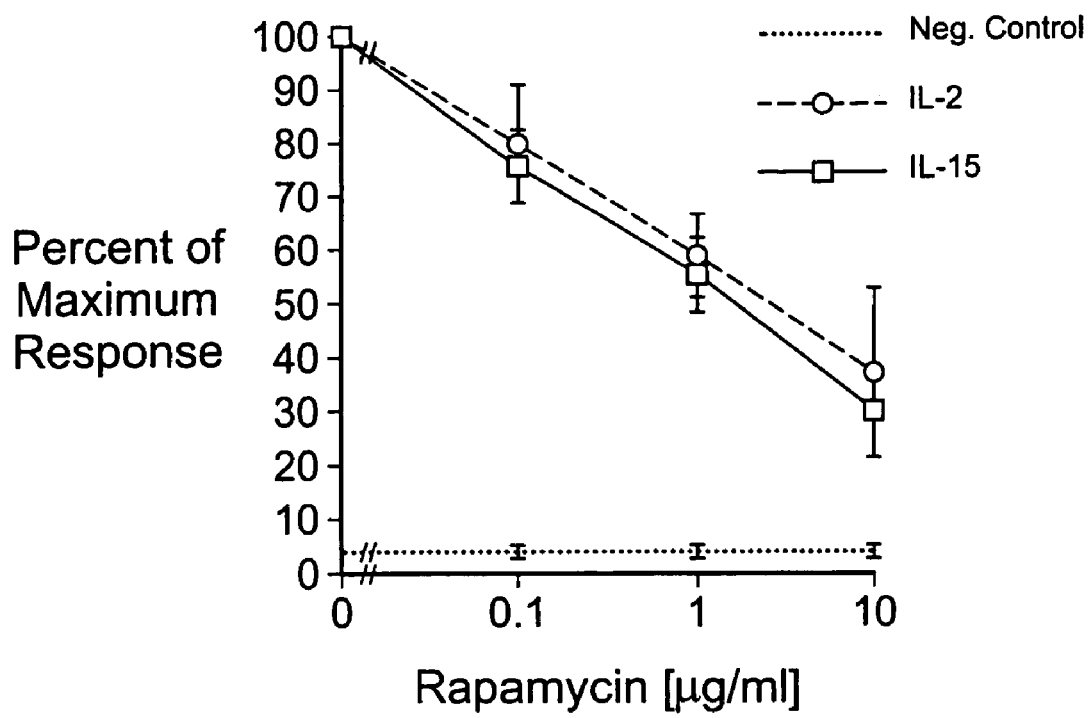
FIG. 10 is a graph depicting the effect of rapamycin on the proliferation of PHA-stimulated PBMCs. Cells were incubated with increasing concentrations of rapamycin for 15 minutes at 37° C., followed by stimulation with IL-2 (○ - - - ○) or IL-15 (□ - - - □) for 38 hours, and a standard proliferation assay was performed. In the control experiment, cells were cultured in media lacking exogenously added cytokines. Error bars indicate the mean±standard deviation.

Tyrosine phosphorylation events are critical for IL-15 stimulated proliferation. Indeed, a direct comparison of the pattern of tyrosine phosphorylation shows that the protein phosphorylation induced by IL-2 is identical to the protein phosphorylation induced by IL-15 (FIG. 10). This indicates that both cytokines stimulate similar, if not identical, protein tyrosine kinases.

IL-2 and IL-15 Stimulated Proliferative Events are Equally Sensitive to Inhibition by Rapamycin To further characterize the signaling events that are mediated by IL-2 and IL-15, the sensitivity of IL-2 and IL-15 induced T cell proliferation to rapamycin, which inhibits IL-2R signal transduction. Rapamycin, a macrolide with potent immunosuppressive activity (Sigal et al., *Annu. Rev. Immunol.* 10:519, 1992; Sehgal et al., *ASHI Quarterly* 15:8, 1991), inhibits IL-2 induced signal transduction prior to or at the level of activation of p70 S6 kinase and cyclin E dependent cdk2 kinase (Price et al., *Science* 257:973, 1992; Bierer et al., *Proc. Natl. Acad. Sci. USA* 87:9231, 1990; Calvo et al., *Proc. Natl. Acad. Sci. USA* 89:7571, 1992; and Chung et al., *Cell* 69:1227, 1992). PHA-stimulated, IL-2-activated cells were washed prior to incubation with rapamycin and cultured with IL-2 or IL-15. Again, the similarity of IL-2 and IL-15 induced T cell proliferative events was evident: the proliferative events stimulated by these two interleukins were equally dose-sensitive to inhibition by rapamycin (FIG. 10). Just as in studies involving genistein (see above), the possibility that rapamycin was toxic to lymphocytes was ruled out by performing standard trypan blue exclusion assays (*Current Protocols in Immunology*, Vol. 3, ed. Coico, R. New York: John Wiley & Sons, 1995). Cell viability after three days of incubation with rapamycin (10 ng/ml) was 8.5%±10% of the control, where no drug was added. Therefore, the observed inhibition of cellular proliferation by rapamycin is due to an inhibition of IL-2 and IL-15 induced signal transduction.

Figure 11:
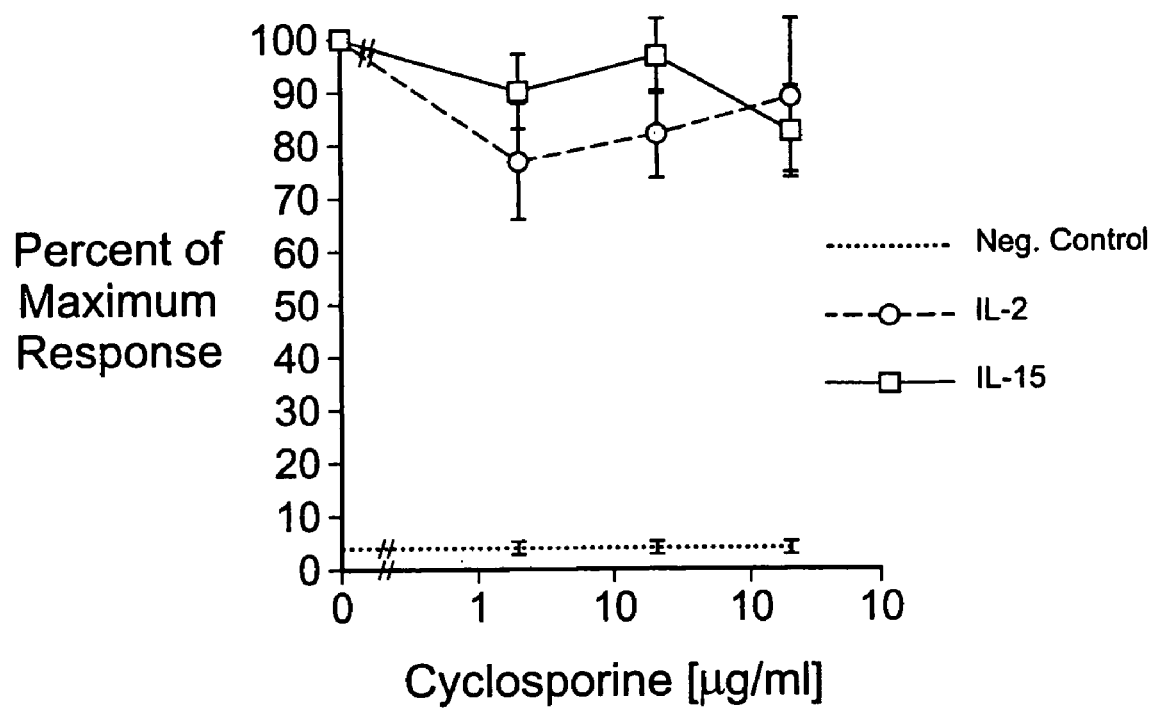
FIG. 11 is a graph depicting the effect of cyclosporin-A on the proliferation of PHA-stimulated PBMCs. The cells were incubated with increasing concentrations of cyclosporine-A for 15 minutes at 37° C., followed by stimulation with IL-2 or IL-15 for 38 hours, and a standard proliferation assay was performed. In the control experiment, cells were cultured in media lacking exogenously added cytokines. Error bars indicate the mean±standard deviation.

The Immunosuppressant Cyclosporin does not Inhibit Either IL-2 or IL-15 Induced Cellular Proliferation The effect of a second immunosuppressant, cyclosporine-A (CsA), on IL-15 induced cell proliferation was also examined. Cyclosporine-A is a peptide that forms complexes with cyclophilin; these complexes bind to and inhibit the enzymatic activity of the cellular phosphate calcineurin, resulting, among other effects, in blockade of IL-2 and IL-2Rα gene transcription (Sigal et al., *Annu. Rev. Immunol.* 10:519, 1992). T cells expressing the tri-molecular IL-2R complex and stimulated with exogenously added IL-2 are not sensitive to CsA (Sigal et al., *Annu. Rev. Immunol.* 10:519, 1992). It has now been shown that CsA does not inhibit IL-15 or IL-2 triggered cellular proliferation (FIG. 11), again revealing similarities between IL-2 and IL-15 induced cellular proliferation.

The doses of CsA used in these studies (to block PHA-induced IL-2 gene expression) were tested in order to provide evidence that a sufficient amount of CsA was being used. CsA (100 ng/ml) completely blocked PHA-induced IL-2 mRNA expression as judged by the results of RT-PCR and competitive PCR techniques, as described before (Lipman et al., *J. Immunol.* 152:5120, 1994). This result confirms the efficacy of CsA in the culture system used herein. Moreover, it discounts the possibility that IL-15 induces IL-2 gene expression that, in turn, could be responsible for T cell proliferation.

The IL-2Rβ Subunit is Critical for both IL-2 and IL-15 Signal Transduction

Figure 12A:
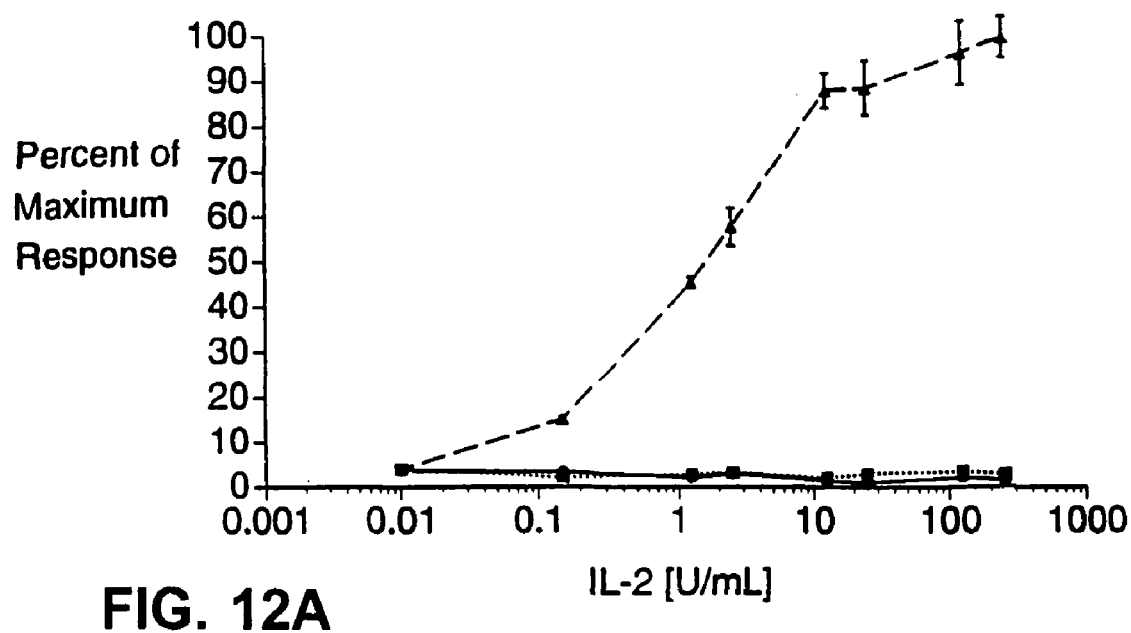
FIGS. 12A and 12B is a pair of graphs depicting the proliferative response of BAF-BO3 cells that express the wild-type IL-2Rβ subunit (WT, ▲ - - - ▲), the mutant IL-2Rβ subunit that lacks serine-rich region S⁻, ■ - - - ■), or a control vector (V, ● - - - ●). The cells were incubated with IL-2 (upper graph) or IL-15 (lower graph) for 38 hours and a standard proliferation assay was performed. Error bars indicate the mean±standard deviation.
Figure 12B:
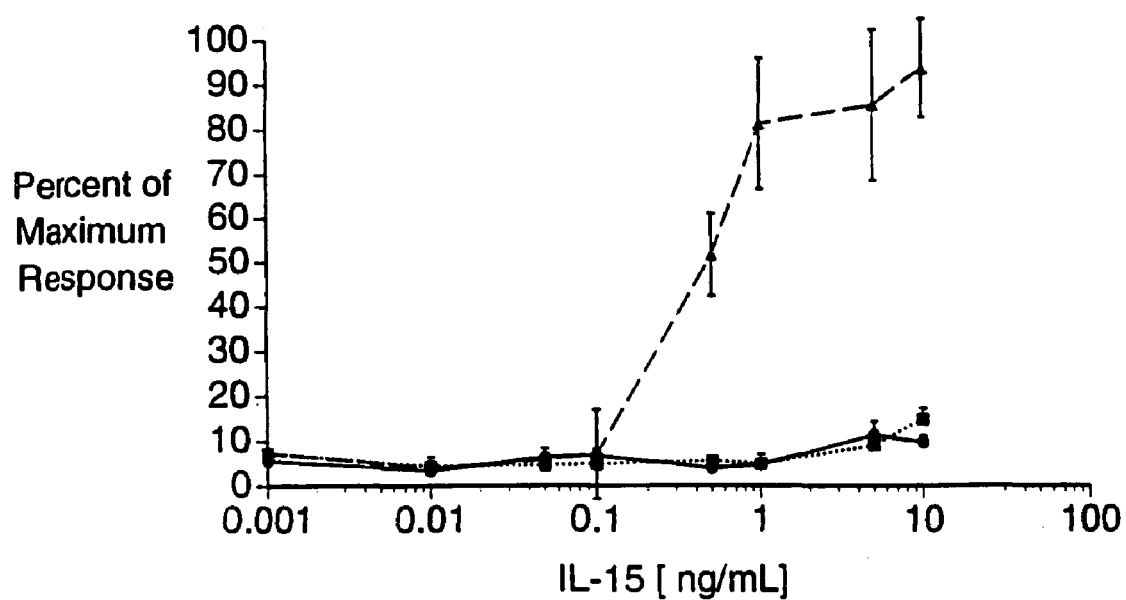

The hypothesis that elements of the IL-2Rβ chain that are required for IL-2 signal transduction are also required for IL-15 signal transduction was tested. Previous studies indicated that BAF-BO3 cells that express endogenous IL-2Rα and IL-2Rγ subunits can be rendered IL-2 dependent upon transfection with cDNA encoding human the IL-2Rβ protein (Hatakeyama et al., *Science* 244:551, 1989). In contrast, BAF-BO3 cells that express a mutant IL-2Rβ protein, which lacks a 71 amino acid serine-rich region, do not respond to IL-2 (Hatakeyama et al., *Science* 252:1523, 1991; Hatakeyama et al., *Science* 244:551, 1989; and Fung et al., *J. Immunol.* 147:1253, 1991). Therefore, the ability of IL-15 to induce the proliferation of IL-2Rαγ$^+$BAF-BO3 cells that express either the wild-type IL-2Rβ subunit or a mutant IL-2Rβ protein that lacks the serine rich region (S$^-$). While both IL-2 and IL-15 stimulate the proliferation of cells that express the wild-type IL-2Rβ subunit, neither cytokine is able to stimulate IL-2Rαγ$^+$ BAF-BO3 cells that express mutant S$^-$ IL-2Rβ subunit (FIG. 12). These results demonstrate that the serine-rich region of the IL-2Rβ subunit is critical for both IL-2 and IL-15 triggered signal transduction.

The serine-rich region of the IL-2Rβ subunit binds several tyrosine kineses including Jak-1 and Syk (Minami et al., *Immunity* 2:89, 1995). The same kinases may play a critical role in both IL-2 and IL-15 signal transduction. Since BAF-BO3 cells cannot express IL-2 (Anderson et al., *J. Biol. Chem.* 270:29862, 1995), even upon stimulation with IL-15, these results indicate that IL-15 induced cellular proliferation does not require induction of IL-2 gene expression.

The experiments performed in this series (see also Lin et al., *Immunity* 2:331, 1995; Anderson et al., *J. Biol. Chem.* 270:29862, 1995) indicate that IL-2 and IL-15 triggered signal transduction use overlapping, perhaps identical, signaling pathways, and that agents that block IL-2 signaling are highly likely to block IL-15 signaling. Although these experiments compared relatively early events in the course of IL-2 and IL-15 intracellular signal transduction, the terminal phase of IL-2 and IL-15 signal transduction are also likely to be quite similar insofar as activation of target cells with IL-2 or IL-15 gives rise to expression of the same DNA binding proteins (Giri et al., *EMBO J.* 13:2822, 1994). These results also suggest that the function of the IL-15Rα and IL-2Rα chain are similar, i.e., that they are most important for cytokine binding affinity and have a negligible role in signal transduction.

Decreasing the viability of activated T cells or blocking the signal transduction pathways activated by IL-2 and IL-15 provides a way to decrease the production of lymphokines and mitogens that contribute to accelerated atherosclerosis, allograft rejection, certain leukemias and other immune-mediated pathologies. When activated, T cells proliferate and express receptors on their cell surface for interleukins. In addition, activated T cells release at least three lymphokines: gamma interferon, B cell differentiation factor II, and IL-3. These lymphokines can produce various undesirable events, such as allograft rejection. In contrast, resting T cells and long-term memory T cells do not express lymphokine receptors. This difference in receptor expression provides a means to target activated immune cells without interfering with resting cells. Molecules designed to recognize some subunit of the IL-15R will recognize activated monocytes/macrophages as well as activated T cells and can be used to selectively inhibit or destroy these cells. Derivatives of IL-15 that bind to an IL-15R subunit but that lack IL-15 activity, either because they block the binding and/or uptake of bona fide IL-15, are useful in the method of the invention. The mutant IL-15 molecule described below provides a working example of such a derivative.

A Mutant IL-15 Polypeptide that Functions as an Antagonist of Wild-Type IL-15

Genetic Construction of Mutant IL-15

The human IL-15 protein bearing a double mutation (Q149D; Q156D) was designed to target the putative sites critical for binding to the IL-2Rγ subunit. The polar, but uncharged glutamine residues at positions 149 and 156 (FIG. 12) were mutated into acidic residues of aspartic acid (FIG. 13) utilizing PCR-assisted mutagenesis. A cDNA encoding the double mutant of IL-15 was amplified by PCR utilizing a synthetic sense oligonucleotide [5'-G GAATTCAACTGGGTGAATGTAATA-3'(SEQ ID NO:1); EcoRI site (underlined hexamer) plus bases 145-[62] and a synthetic antisense oligonucleotide [5'-CG GGATCCTCAAGAAGTGTTGATGAACATGT CGACAATATGTACAAAACTGTCCAAAAAT-3' (SEQ ID NO:3); BamHI site (underlined hexamer) plus bases 438-489; mutated bases are singly underlined]. The template was a plasmid containing cDNA that encodes human FLAG-HMK-IL-15. The amplified fragment was digested with EcoRI/BamHI and cloned into the pAR(DRI)59/60 plasmid digested with EcoRI/BamRI as described (LeClair et al., *Proc. Natl. Acad. Sci. USA* 89:8145, 1989). The presence of a mutation at residue 156 was confirmed by digestion with SalI; the mutation introduces a new SalI restriction site. In addition, mutations were verified by DNA sequencing, according to standard techniques. The FLAG-HMK-IL-15 (Q149D; Q156D) double mutant protein was produced, purified, and verified by sequencing as described above for the FLAG-HMK-IL-15 wild-type protein.

Using this same strategy, mutants that contain only a single amino acid substitution, either at position 149 or at position 156 were prepared. As described above, these positions (149 and 156) correspond to positions 101 and 108, respectively, in the mature IL-15 polypeptide, which lacks a 48-amino acid signal sequence.

Similarly, this strategy can be used to incorporate any other amino acid in place of the glutamine residues at positions 149 or 156 or to introduce amino acid substitutions at positions other than 149 and/or 156.

Proliferation of BAF-BO3 Cells in the Presence of IL-15 Related Proteins

In order to study the effect of various IL-15 related proteins, including the mutant polypeptides described above, on the proliferation of BAF-BO3 cells, the following experiment was performed in vitro. BAF-BO3 cells were transfected in culture with DNA from either pRcCMV-IL-2Rβ or pRcCMV-0. These plasmids differ in that pRcCMV-IL-2Rβ contains an insert encoding the human IL-2Rβ subunit and pRcCMV-0 does not. Following transfection, the cells were washed and treated with either: (1) unsupplemented medium ("none"), (2) IL-2, (3) IL-3 rich WEHI cell supernatant (WEHI), (4) FLAG-HMK-IL-15, (5) FLAG-HMK-IL-15 Q149D single mutant (149), (6) FLAG-HMK-IL-15 Q156D double mutant (DM), (7) IL-15, or (8) IL-15+FLAG-HMK-IL-15 Q149D Q156D double mutant (FIG. 15). Cells transfected with pRcCMV-0 DNA, did not proliferate in response to any stimulus except WEHI cell supernatant. In contrast, following transfection with pRcCMV-IL-2Rβ DNA, IL-2, WEHI cell supernatant, FLAG-HMK-IL-15, FLAG-HMK-IL-15 Q149D single mutant, and IL-15 stimulated cellular proliferation. The IL-2Rβ expressing cells did not proliferate in response to the double mutant IL-15. The double mutant IL-15 polypeptide may inhibit BAF-BO3 proliferation in a dose-dependent manner: addition of 30 μl (approximately 50 μg/ml) of the double mutant IL-15 inhibited proliferation more completely than did addition of 20 μL of the same concentration of the double mutant IL-15.

Proliferation of PHA-Stimulated Human PBMCs in the Presence of IL-15 Related Proteins Human PBMCs prestimulated with PHA (2 μg/ml) for 72 hours were washed and cultured in the presence of IL-15 related proteins including: (1) the IL-15 double mutant, FLAG-HMK-IL-15-Q149D-Q156D, (2) the IL-15 single mutant, FLAG-HMK-IL-15-Q149D, or (3) the IL-15 single mutant, FLAG-HMK-IL-15-Q156D (FIG. 16). Medium without an IL-15 related polypeptide served as a control. The proliferative response was then assessed.

FACS Analysis of PHA-Activated Human PBMCs Stained with FLAG-HMK-IL-15-Double Mutants The ability of the FLAG-HMK-IL-15 double mutant polypeptide to bind PHA-activated human PBMCs was demonstrated as follows. PHA-activated PBMCs were washed and incubated with medium alone, or with the FLAG-HMK-IL-15 double mutant. The cells were then incubated with an anti-FLAG biotinylated antibody and stained with streptavidin conjugated to RED670. The stained cells were analyzed by flow cytometry (FIG. 17).

FACS Analysis of Leukemic Cell Lines Stained with Wild-Type FLAG-HMK-IL-15

In a series of experiments similar to those above, the ability of the wild-type FLAG-HMK-IL-15 polypeptide to bind leukemia cells was shown. The cells treated were obtained from the leukemic cell lines MOLT-14, YT, HuT-102, and from cell lines currently being established at Beth Israel Hospital (Boston, Mass.), and named 2A and 2B. The cultured cells were washed and incubated with either medium alone or with medium containing the FLAG-HMK-IL-15 wild-type polypeptide (FIG. 18). The cells were then incubated with the biotinylated anti-FLAG antibody and stained with RED670-conjugated streptavidin. The stained cells were analyzed by flow cytometry.

Genetic Construction of Additional Mutant IL-15 Chimeric Polypeptides

In addition to the FLAG-HMK-IL-15 chimera, which provides the mutant IL-15 with an antigenic tag, numerous other polypeptides can be linked to any mutant of IL-15. For example, mutant IL-15 can be linked to serum albumin or to the Fc fragment of the IgG subclass of antibodies, according to the following method.

Genetic Construction of Mutant IL-15/Fc–– cDNA for Fcγ2a can be generated from mRNA extracted from an IgG2a secreting hybridoma using standard techniques with reverse transcriptase (MMLV-RT; Gibco-BRL, Grand Island, N.Y.) and a synthetic oligo-dT (12-18) oligonucleotide (Gibco BRL). The mutant IL-15 cDNA can be amplified from a plasmid template by PCR using IL-15 specific synthetic oligonucleotides.

The 5' oligonucleotide is designed to insert a unique NotI restriction site 40 nucleotides 5' to the translational start codon, while the 3' oligonucleotide eliminates the termination codon and modifies the C-terminal Ser residue codon usage from AGC to TCG to accommodate the creation of a unique BamHI site at the mutant IL-15/Fc junction. Synthetic oligonucleotides used for the amplification of the Fcγ2a domain cDNA change the first codon of the hinge from Glu to Asp in order to create a unique BamHI site spanning the first codon of the hinge and introduce a unique XbaI site 3' to the termination codon. The Fc fragment can be modified so that it is non-lytic, i.e., not able to activate the complement system. To make the non-lytic mutant IL-15 construct (mIL-15/Fc––), oligonucleotide site directed mutagenesis is used to replace the C'1q binding motif Glu318, Lys320, Lys322 with Ala residues. Similarly, Leu235 is replaced with Glu to inactivate the FcγR I binding site. Ligation of cytokine and Fc–– components in the correct translational reading frame at the unique BamHI site yields a 1,236 basepair open reading frame encoding a single 411 amino acid polypeptide (including the 18 amino acid IL-15 signal peptide) with a total of 13 cysteine residues. The mature secreted homodimeric IL-15/Fc–– is predicted to have a total of up to eight intramolecular and three inter-heavy chain disulfide linkages and a molecular weight of approximately 85 kDa, exclusive of glycosylation.

Expression and Purification of mIL-15 Fc Fusion Proteins

Proper genetic construction of both mIL-15/Fc++, which carries the wild-type Fcγ2a sequence, and mIL-15/Fc–– can be confirmed by DNA sequence analysis following cloning of the fusion genes as NotI-XbaI cassettes into the eukaryotic expression plasmid pRc/CMV (Invitrogen, San Diego, Calif.). This plasmid carries a CMV promoter/enhancer, a bovine growth hormone polyadenylation signal, and a neomycin resistance gene for selection with G418. Plasmids carrying the mIL-15/Fc++ or mIL-15/Fc–– fusion genes are transfected into Chinese hamster ovary cells (CHO-K1, available from the American Type Culture Collection) by electroporation (1.5 kV/3 μF/0.4 cm/PBS) and selected in serum-free Ultra-CHO media (BioWhittaker Inc., Walkerville, Md.) containing 1.5 mg/ml of G418 (Geneticin, Gibco BRL). After subcloning, clones that produce high levels of the fusion protein are selected by screening supernatants from IL-15 by ELISA (PharMingen, San Diego, Calif.). mIL-15/Fc fusion proteins are purified from culture supernatants by protein A sepharose affinity chromatography followed by dialysis against PBS and 0.22 μm filter sterilization. Purified proteins can be stored at –20° C. before use.

Western blot analysis following SDS-PAGE under reducing (with DTT) and non-reducing (without DTT) conditions can be performed using monoclonal or polyclonal anti-mIL-15 or anti Fcγ primary antibodies to evaluate the size and isotype specificity of the fusion proteins.

Standardization of the Biological Activity of Recombinant Mutant IL-15 and mIL-15/Fc–– Proteins Using the RT-PCR strategy and 5' NotI sense oligonucleotide primer described above, mutant IL-15 cDNA with an XbaI restriction site added 3' to its native termination codon, can be cloned into pRc/CMV. This construct is then transiently expressed in COS cells (available from the American Type Culture Collection). The cells may be transfected by the DEAE dextran method and grown in serum-free UltraCulture™ media (BioWhittaker Inc.). Day 5 culture supernatant is sterile filtered and stored at –20° C. for use as a source of recombinant mutant IL-15 protein (rmIL-15).

Mutant IL-15/Fc–– and rmIL-15 mutant protein concentrations can be determined by ELISA as well as by bioassay, as described (Thompson-Snipes et al., *J. Exp. Med.* 173:507, 1991).

The functional activity of mutant IL-15/Fc–– can be assessed by a standard T cell proliferation assay, as described above.

Determination of mIL-15/Fc–– or mIL-15/Fc++ Circulating Half-Life

Serum concentration of mIL-15/Fc or mIL-15/Fc++ fusion proteins can be determined over time following a single intravenous injection of the fusion protein. Serial 100 μl blood samples can be obtained by standard measures at intervals of 0.1, 6, 24, 48, 72, and 96 hours after administration of mutant IL-15/Fc–– protein. Measurements employ an ELISA with a mIL-15 mAb as the capture antibody and horseradish peroxidase conjugated to an Fc"2a mAb as the detection antibody, thus assuring this assay is specific for only the mutant IL-15/Fc––.

IL-15 Mutants in the Treatment of Arthritis

Rheumatoid arthritis (RA) is a T cell dependent autoimmune disease in which mononuclear cells infiltrate the joints, causing inflammation and progressive destruction of articular cartilage and bone. Therapies for alleviating RA have been tested in the murine type II collagen-induced arthritis (CIA) model (see, e.g., Courtenay et al., *Nature* 283:666-668, 1980).

Direct contact between collagen type II (CII) immune T cells and monocytes or T cells and synoviocytes leads to the production of proinflammatory cytokines, such as IL-1β and TNF-α (Burger et al., *Arthritis and Rheumatism* 41:1748-1759, 1998; Rezzonico et al., *J. Biol. Chem.* 30:18720-18728, 1998; Vey et al., *J. Immunol.* 149:2040-2046, 19??; Isler et al., *Eur. Cytokine. Netw.* 4:15-23, 1993) and metalloproteinases (Miltenburg et al., *J. Immunol.* 154:2655-2667, 1995). TNFα is strongly implicated in the pathogenesis of CIA and clinical RA. In patients with RA, T cells that infiltrate synovia, monocytes, and macrophages produce high levels of TNFα (Akatsuka et al., *Microbiol. Immunol.* 41:367-370, 1997; Feldmann et al., *Ann. Rev. Immunol.* 14:397-440, 1996). The success of therapeutic strategies that neutralize TNFα in the murine CIA model and in clinical RA also indicates that TNFα plays a crucial role in the pathogenesis of arthritis (Knight et al., *Mol. Immunol.* 30:1443-1453, 1993; Wooley et al., *J. Immunol.* 151:6602-6607, 1993; Williams et al., *Immunol.* 84:433-439, 1995; Elliott et al., *Lancet* 344:1105-1110, 1994; Elliott et al., *Lancet* 344:1125-1127, 1994; Moreland et al., *N. Engl. J. Med.* 337:141-147, 1997).

We have found that DBA/1 mice treated with an IL-15 mutant/Fcγ2a protein, which acts in part as a long lived, high affinity IL-15 receptor (IL-15R) antagonist, have a markedly decreased incidence of RA-like collagen type II arthritis. In addition, those mice that do develop arthritis experience markedly less intense symptoms. Surprisingly, the benefits of IL-15R antagonists persist long after the treatment is discontinued. As shown by the experiments described below, expression of the proinflammatory cytokines IL-1β and TNFα was dramatically decreased in IL-15 mutant/Fcγ2a-treated mice, and histological analyses confirmed that treatment with IL-15 mutant/Fcγ2a protects joints from leukocytic infiltration. These results support the hypothesis that IL-15 and IL-15R-positive mononuclear leukocytes play a major role in the inflammatory processes that cause arthritis and demonstrate the efficacy of IL-15R antagonists in treating this condition.

Expression and Purification of IL-15 Mutant/Fcγ2c Protein

NS 1 cells, a B cell line available from the American Type Culture Collection, were transfected with a plasmid carrying a fusion gene encoding human IL-15 linked to murine Fcγ2a cDNA. The plasmid was constructed as described above. (see "Genetic Construction of mutant IL-15") The transfected cells were cloned and cultured in serum-free Ultraculture medium (BioWhittaker Inc., Walkersville, Md.) containing 100 μg/ml Zeocin (Invitrogen, San Diego, Calif.). IL-15 mutant/Fcγ2a fusion proteins were purified from the culture supernatant from high producing clones by protein A-Sepharose affinity chromatography (Pharmacia, Piscataway, N.J.). The expressed protein was dialyzed against PBS and sterilized by passage through a 0.22 μm filter. Purified protein was stored at −20° C.

Induction of Collagen-Induced Arthritis

Male DBA/1 mice, 8-9 weeks old, were obtained from The Jackson Laboratory (Bar Harbor, Me.) and used in this series of experiments. CII (1 mg) derived from chicken sternal cartilage (Sigma Chemical Co., St. Louis, Mo.) was dissolved by placing it in 0.1 M acetic acid (1 ml) at 4° C. for 24 hours and then emulsified with an equal volume of Freund's complete adjuvant (CFA; Sigma Chemical Co., St. Louis, Mo.; see, Courtenay et al., *Nature* 283:666-668, 1980). To induce CIA, 300 μl of the emulsion was injected intradermally at the base of the tail of DBA/1 mice at day 0. On day 21, the animals received a second injection; 200 μg of CII was injected intraperitoneally.

Treatment for Arthritis

Twenty-one days following the last injection of CII, animals were divided into two groups. The first group received daily intraperitoneal injections of IgG2a (Becton Dickinson, San Jose, Calif.) at a concentration of 1.5 μg/mouse, and the second group received daily intraperiotoneal injections of IL-15 mutant/Fcγ2a protein at a final concentration of 1.5 μg/mouse. Treatment was continued until animals were sacrificed or a maximum of 10 days.

Mice were evaluated every day for arthritis based on the following arthritis severity index: grade 0—no swelling; grade 1—mild swelling or erythema; grade 2—pronounced edema or redness of the paw or of several digits; grade 3—severe swelling of the entire paw or ankylosis. All four limbs of each animal were graded, resulting in a maximum clinical score of 12/animal.

Six animals were sacrificed 21 days after immunization. Nineteen IgG2a-treated and eighteen IL-15 mutant/Fcγ2a-treated mice were sacrificed 4 days, 7 days, and 21 days after the onset of arthritis (25, 28, and 42 days post-immunization, respectively). All remaining IgG2a- and IL-15 mutant/Fcγ2a-treated mice were sacrificed on day 42.

Histology

The animals' paws were removed post-mortem, fixed in 1% paraformaldehyde for three days, and then decalcified in 5% EDTA for two weeks. The tissue was then embedded in paraffin and sectioned. Sagittal serial sections were stained with hematoxylin and eosin before examination.

Measurement of Serum Cytokines

Serum levels of TNFα and IL-1β were assayed by ELISA (R&D Systems, Minneapolis, Minn.) according to the manufacturer's instructions. Lower limits of detection were at 5-10 pg/ml for TNFα and at 10 pg/ml for IL-1β.

mRNA Analysis

Tissue samples were homogenized with a polytron (Kinematika, Switzerland), and total cellular RNA was extracted by RNASTAT 60™ (Tel Test, Friendswood, Tex.). The RNA samples were processed according to the manufacturer's instructions. RT-PCR was performed as described in Strehlau et al. (*Proc. Natl. Acad. Sci. USA* 94:695-700, 1997). Briefly, 1 μg of total RNA isolated from individual joint samples was reverse transcribed into cDNA utilizing M-MLV reverse transcriptase (Promega, Madison, Wis.). The cDNA was then amplified in a 25 μl reaction volume containing 3 μl of cDNA samples, 2.5 mM of each deoxynucleotide triphosphate, 1.5 mM $MgCl_2$, 50 mM KCl, 10 mM Tris-HCl (pH 8.3), 5 U/μl Taq DNA polymerase. (Perkin Elmer, Roche Molecular Systems, Inc., Branchburg, N.J.), and 190 ng of sense and anti-sense primers. The specific primers used for hybridization to murine INF-γ, IL-10, TCR Cβ and GAPDH cDNA, the latter as an internal control, were described in Steiger et al., (*J. Immunol.* 155:489-498, 1995). The primers used to amplify murine TNFα were 5'-CCAACGGCATGGATCTCAAA-GAC-3' (sense; SEQ ID NO:9) and 5'-TCACTGTCCCAG-CATCTTGTGTTTC-3' (antisense; SEQ ID NO:10). The primers used to amplify murine IL-1β were 5'-TGCACTA-CAGGCTCCGAGATGAAC-3' (sense; SEQ ID NO:11) and 5'-CATCAGAGGCAAGGAGGAAACACAG-3' (antisense; SEQ ID NO:12). The PCR was performed in the GeneAmp™ PCR system 2400 (Perkin Elmer, Cetus, Norwalk, Conn.) under the following conditions: denaturation at 94° C. for 30 seconds; annealing at 60° C. for INFγ, at 62° C. for IL-10, at 55° C. for GAPDH, and at 59° C. for TNFα and IL-1β; and extension at 72° C. for 45 seconds. Forty cycles were made. A negative control, the omission of cDNA in the PCR reaction mixture, was included for each PCR amplification. After amplification, the samples (10 μl) were separated on ethidium bromide-containing 1.5% agarose gels. The DNA was visualized and photographed using an ultraviolet transilluminator (Gel Doc 1000™, Bio Rad, Hercules, Calif.).

Measurement of Serum Anti-CII Antibody Levels

A sandwich ELISA was used to assess levels of serum specific IgG1 and IgG2a to CII (see, Kageyama et al., *J. Immunol.* 161:1542-1548, 1998). The serum samples were collected 21, 25, 28, and 42 days after primary immunization and frozen at −70° C. Native chicken CII was dissolved in 0.1 M acetic acid at 1 mg/ml and diluted with 0.1 M sodium bicarbonate at 0.1 μg/ml (pH 9.6). 96-well plates (Costar, Cambridge, Mass.) were coated with 100 μl of CII Ag solution and incubated overnight at 4° C. Plates were then washed three times with TBS (20 mM Tris pH 8.0, 150 mM NaCl) containing 0.05% Tween 20 and subsequently blocked with 170 μl of 10% BSA in TBS for 2 hours at room temperature. Plates were washed three times and then incubated with 100 μl/well of serum serially diluted in TBS-Tween 20/10% BSA for 1 hour at 37° C. After three washes, 100 μl of peroxidase conjugate (1:500 dilution) was added to detect IgG1 subclass antibodies. The peroxidase conjugate was applied for 30 minutes at 37° C. After washing three times, 100 μl of O-phenylenediamine (0.5 mg/ml) dissolved in 0.1 M citric acid and 0.2 M $Na_2HPO_4$ containing 0.001% $H_2O_2$ was added. The reaction was stopped by addition of 0.25 $NH_2SO_4$ (50 μl/well). Quantitation was established by an ELISA reader (at 490 nm).

Treatment with IL-15 Mutant/Fcγ2a Delays the Onset and Diminishes the Severity of CIA DBA/1 mice immunized with an intradermal injection of CII and challenged 21 days later with CII developed severe arthritis. Daily treatment with the IL-15 mutant/Fcγ2a protein for a maximum of 10 days delayed the onset of disease and decreased the severity and incidence of CIA (relative to mice receiving an IgG control protein). Data analysis was performed using a Kaplan-Meier cumulative plot for even free of disease and comparison between groups was performed using a logrank test for event time (Statview 5.1, SAS Institute Inc., Cory, N.Y.)*$p<0.01$.

The severity of arthritis was monitored by a macroscopic score (and, as described above, was based on the following arthritis severity index: grade 0—no swelling; grade 1—mild swelling or erythema; grade 2—pronounced edema or redness of the paw or of several digits; grade 3—severe swelling of the entire paw or ankylosis). A marked reduction in clinical score an in the number of arthritic paws was observed throughout the treatment period. Remarkably, the beneficial effect of the IL-15 mutant/Fcγ2a protein treatment persisted following cessation of treatment. Mice were killed at various times after the onset of clinical arthritis, and the unaffected and affected paws were examined. Histological analyses showed that the marked tissue infiltration of mononuclear cells observed in sections of IgG-treated mice was vastly decreased in IL-15 mutant/Fcγ2a-treated mice.

The Effect of IL-15 Mutant/Fcγ2a on Cytokine Expression in Joint Tissue.

The effect of IL-15 mutant/Fcγ2a treatment on the expression of TNFα and IL-1β was analyzed because these cytokines play a central role in joint inflammation through the induction of other proinflammatory cytokines and metalloproteinases (Dayer et al., *J. Exp. Med.* 162:2163-2168, 1985; MacNaul et al., *J. Biol. Chem.* 265:17238-17245, 1990).

Mice immunized with CII and treated with either control IgG or IL-15 mutant/Fcγ2a were sacrificed at day 25, day 28, day 42, or day 68. Expression of IL-1β and TNFα was examined at the transcriptional and translational levels. Sera were processed for protein quantification and joints for mRNA analyses and immunostaining. IL-1β was detected in 40% of IgG-treated mice but in only 10% of IL-15 mutant/Fcγ2a-treated mice. TNFα protein was never detected in the sera. In parallel, we assessed cytokine mRNA expression from joint tissues using RT-PCR and immunostaining. Both TNFα and IL-1β are massively expressed in joints of mice treated with control protein, but these cytokines were expressed in only a minority of mice treated with the IL-15 related fusion protein. These data demonstrate that the IL-15 mutant/Fcγ2a protein powerfully diminishes expression of proinflammatory cytokines. Both IFNγ and IL-10 were expressed in some control-treated mice, but these cytokines were detected in a minority of IL-15 antagonist-treated mice.

The Anti-CII Humoral Response is not Altered by IL-15 Antagonist.

To determine whether treatment with IL-15 mutants inhibits anti-CII antibody production, serum from both experimental and control animals was obtained 25, 28, and 42 days following immunization. Anti-CII antibody levels varied greatly between mice. The variation was independent of the day of collection and no significant difference in the expression of IgG1 or IgG2a subtype antibodies was observed between the two treatment groups. These data indicate that treatment with the IL-15 mutant/Fcγ2a protein does not produce clinical improvement through an effect upon anti-CII antibody production.

The Effect of IL-15 mutant/Fcγ2a on the Intraarticular T Cell Response.

To determine if the T cell response was altered by IL-15 mutant/Fcγ2a treatment, we analyzed TCR Cβ gene expression in joint tissues of control-treated or IL-15 mutant-protein-treated mice by QRT-PCR. As the common chain of TCRβ is constitutively expressed by T cells, a decrease in the number of T cells present in the joint should be accompanied by a decrease in the abundance of TCR Cβ gene transcripts within the tissue. The magnitude of intraarticular TCR Cβ gene expression is decreased in IL-15 mutant/Fcγ2a-treated mice as compared to control IgG-treated mice. These results indicate that treatment with IL-15 related fusion proteins inhibits: (1) T cells infiltration of the inflammatory site or (2) proliferation of T cells within the joint tissues.

What is claimed is:

1. A substantially pure mutant IL-15 polypeptide, wherein the mutant IL-15 polypeptide comprises an amino acid sequence that is at least 90% identical to SEQ ID NO:6 and wherein the mutant IL-15 polypeptide comprises a mutation at position 149.

2. The mutant IL-15 polypeptide of claim 1, wherein the amino acid sequence is at least 95% identical to SEQ ID NO:6.

3. The mutant IL-15 polypeptide of claim 1, wherein the amino acid sequence is at least 98% identical to SEQ ID NO:6.

4. The mutant IL-15 polypeptide of claim 1, wherein the amino acid sequence comprises an amino acid substitution relative to SEQ ID NO:6.

5. The mutant IL-15 polypeptide of claim 4, wherein the amino acid sequence comprises only one or more amino acid substitutions relative to SEQ ID NO:6.

6. The mutant IL-15 polypeptide of claim 1, wherein the amino acid sequence comprises an amino acid addition or deletion relative to SEQ ID NO:6.

7. The mutant IL-15 polypeptide of claim 6, wherein the amino acid sequence comprises only one or more amino acid additions or one or more amino acid deletions relative to SEQ ID NO:6.

8. The mutant IL-15 polypeptide of claim 1, wherein the mutation at position 149 is a substitution mutation.

9. The mutant IL-15 polypeptide of claim 8, wherein the substitution is a substitution of aspartic acid for glutamine.

10. The mutant IL-15 polypeptide of claim 1, wherein the mutant IL-15 polypeptide further comprises a mutation at position 156.

11. The mutant IL-15 polypeptide of claim 10, wherein the mutation at position 156 is a substitution mutation.

12. The mutant IL-15 polypeptide of claim 11, wherein the substitution is a substitution of aspartic acid for glutamine.

13. The mutant IL-15 polypeptide of claim 1, wherein the mutant IL-15 polypeptide inhibits cellular proliferation, tyrosine phosphorylation or cytokine expression relative to that which would normally occur when wild-type IL-15 (SEQ ID NO:6) specifically binds to an IL-15 receptor complex.

14. The mutant IL-15 polypeptide of claim 1, further comprising an antigenic tag.

15. The mutant IL-15 polypeptide of claim 14, wherein the antigenic tag is a FLAG sequence comprising Asp-Tyr-Asp-Asp-Asp-Lys (SEQ ID NO:4).

16. The mutant IL-15 polypeptide of claim 1, further comprising an amino acid sequence that increases the circulating half-life of the mutant IL-15 polypeptide.

17. The mutant IL-15 polypeptide of claim 16, wherein the amino acid sequence that increases the circulating half-life of the mutant IL-15 polypeptide is an Fc region of an IgG molecule lacking an IgG variable region.

18. The mutant IL-15 polypeptide of claim 17, wherein the Fc region is lytic.

19. The mutant IL-15 polypeptide of claim 17, wherein the Fc region is non-lytic.

20. A substantially pure mutant of a mature IL-15 polypeptide, wherein the mutant comprises an amino acid sequence that is at least 90% identical to the sequence represented by residues 49-162 of SEQ ID NO:6 and wherein the mutant IL-15 polypeptide comprises a mutation at position 149.

* * * * *